(12) United States Patent
Peeters et al.

(10) Patent No.: US 10,598,583 B1
(45) Date of Patent: Mar. 24, 2020

(54) COMPACT BLOOD HEMATOCRIT SENSING DEVICE

(71) Applicant: Verily Life Sciences LLC, Mountain View, CA (US)

(72) Inventors: Eric Peeters, Mountain View, CA (US); Benjamin David Krasnow, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 239 days.

(21) Appl. No.: 15/600,116

(22) Filed: May 19, 2017

Related U.S. Application Data

(60) Provisional application No. 62/343,833, filed on May 31, 2016.

(51) Int. Cl.
*A61B 5/00* (2006.01)
*G01N 15/05* (2006.01)
(Continued)

(52) U.S. Cl.
CPC ......... *G01N 15/05* (2013.01); *A61B 5/15003* (2013.01); *A61B 5/150099* (2013.01);
(Continued)

(58) Field of Classification Search
CPC ............ A61B 5/15003; A61B 5/15099; A61B 5/150022; A61B 5/150053;
(Continued)

(56) References Cited

U.S. PATENT DOCUMENTS

| 6,128,518 A | 10/2000 | Billings et al. |
| 6,766,191 B1 | 7/2004 | Billings et al. |

(Continued)

FOREIGN PATENT DOCUMENTS

| EP | 0417796 B1 | 9/1990 |
| WO | 2001088521 A1 | 11/2001 |
| WO | 2006017446 A1 | 2/2006 |

OTHER PUBLICATIONS

Muller et al., "Influence of Hematocrit and Platelet Count on Impedance and Reactivity of Whole Blood for Electrical Aggregometry", Journal of Pharmacological and Toxicological Methods, vol. 34, No. 1, Sep. 1995, pp. 17-22.

(Continued)

*Primary Examiner* — Max F Hindenburg
(74) *Attorney, Agent, or Firm* — McDonnell Boehnen; Hulbert & Berghoff LLP

(57) ABSTRACT

Compact devices are provided to measure hematocrit of a blood sample. These devices include first and second chambers that receive respective portions of a blood sample via respective filters. The material of the filters prevents passage of red blood cells while permitting passage of blood plasma. One of the filters has one or more holes to permit the passage of whole blood. Thus, when an example device is presented with a sample of blood, one of the chambers contains whole blood and the other contains blood from which the red blood cells have been filtered. Electrodes in each of the chambers can then be used to detect the impedances of the whole blood and the filtered blood, and the detected impedances can be used to determine a hematocrit of the sample of blood.

20 Claims, 11 Drawing Sheets

(51) Int. Cl.
*A61B 5/15* (2006.01)
*G01N 33/49* (2006.01)
*G01N 27/02* (2006.01)
*G01N 15/00* (2006.01)

(52) U.S. Cl.
CPC .. *A61B 5/150251* (2013.01); *A61B 5/150755* (2013.01); *G01N 27/02* (2013.01); *G01N 33/49* (2013.01); *G01N 2015/0065* (2013.01); *G01N 2015/055* (2013.01)

(58) Field of Classification Search
CPC ........ A61B 5/150213; A61B 5/150251; A61B 5/15029; A61B 5/15115; A61B 5/1411; A61B 5/14532; G01N 15/05; G01N 2015/055
See application file for complete search history.

(56) References Cited

U.S. PATENT DOCUMENTS

| | | | |
|---|---|---|---|
| 8,271,085 B2 | 9/2012 | Lippert et al. | |
| 9,033,898 B2 * | 5/2015 | Chickering, III | A61B 5/1411 600/573 |
| 9,228,995 B2 | 1/2016 | Yang et al. | |
| 9,295,417 B2 * | 3/2016 | Haghgooie | A61B 5/1411 |
| 9,380,972 B2 * | 7/2016 | Fletcher | A61B 5/1411 |
| 9,408,568 B2 * | 8/2016 | Fletcher | A61B 5/1411 |
| 2004/0021469 A1 * | 2/2004 | Blomberg | G01N 33/491 324/434 |
| 2014/0231273 A1 | 8/2014 | McColl et al. | |
| 2015/0068926 A1 | 3/2015 | Ainger et al. | |
| 2015/0087944 A1 * | 3/2015 | Levinson | A61B 5/1438 600/365 |
| 2016/0256095 A1 * | 9/2016 | Krasnow | A61B 5/150099 |

OTHER PUBLICATIONS

Cha K. et al., "An electronic method for rapid measurement of haematocrit in blood samples", May 1994, pp. 129-137, Abstract.

Trebbels D., "Capacitive on-line hematocrit sensor design based on impedance spectroscopy for use in hemodialysis machines", IEEE Eng. Med., Biol. Soc., 2009, pp. 1208-1211, Abstract.

\* cited by examiner

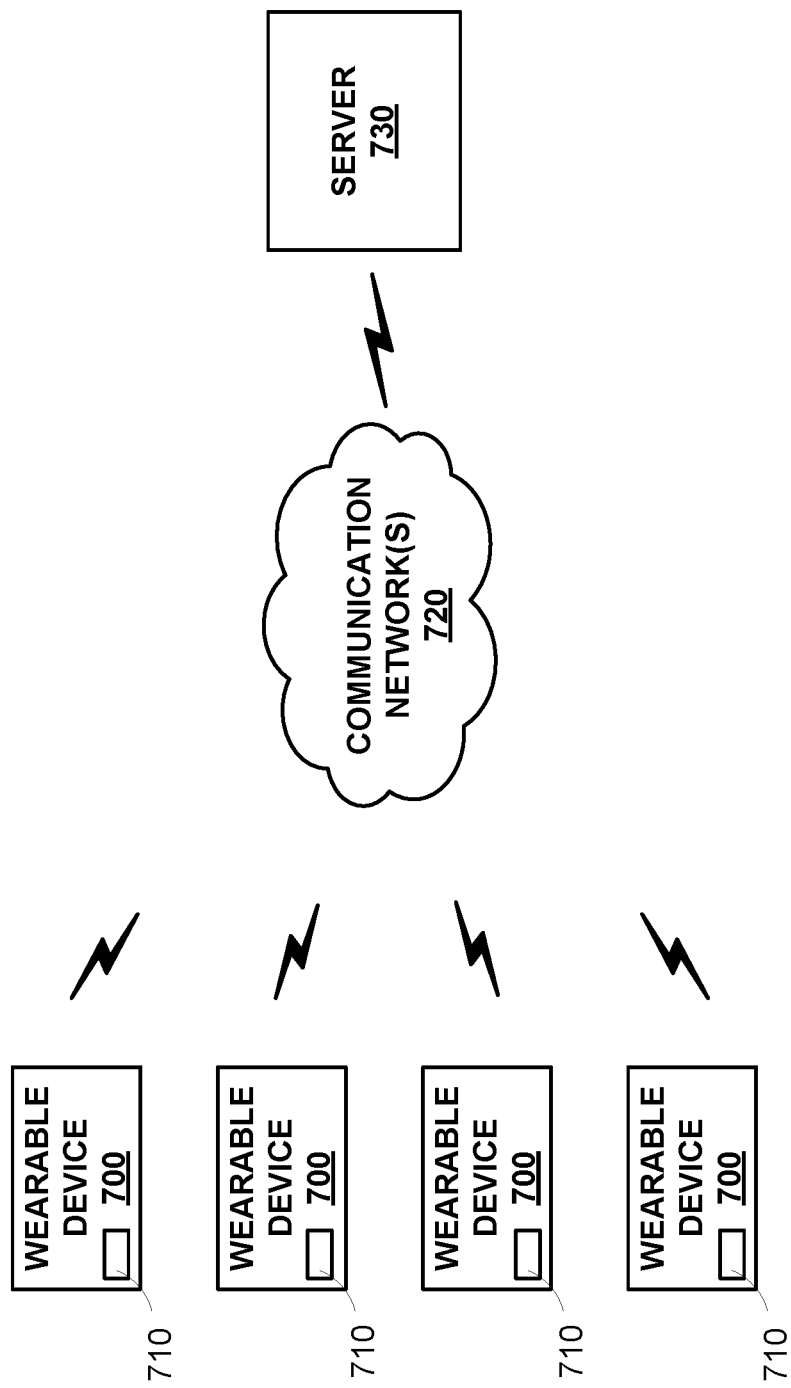

COMPACT BLOOD HEMATOCRIT SENSING DEVICE

CROSS-REFERENCE TO RELATED APPLICATION

This application claims the benefit of and incorporates by reference the content of U.S. Provisional Pat. App. No. 62/343,833, filed May 31, 2016.

BACKGROUND

Unless otherwise indicated herein, the materials described in this section are not prior art to the claims in this application and are not admitted to be prior art by inclusion in this section.

Hematocrit is a property of blood that represents the percent of the blood volume that is taken up by red blood cells. Hematocrit can be used as a diagnostic indicator, e.g., to determine that an individual is experiencing a disease or disorder. A detected hematocrit can be used to control a dose of a drug or to provide some other treatment, e.g., to control a dose of erythropoietin provided to a patient to counteract the effects of chemotherapy on the patient's hematocrit. Hematocrit may be detected by centrifuging a sample of blood using optical methods or other means to detect an amount of compacted red blood cells in the sample. Hematocrit may be detected via other methods.

SUMMARY

Some embodiments of the present disclosure provide a system including: (i) a conduit; (ii) a first filter in fluid communication with the conduit, wherein the first filter includes a material that blocks passage of red blood cells; (iii) a second filter in fluid communication with the conduit, wherein the second filter includes a material that blocks passage of red blood cells, and wherein the second filter has at least one hole through which red blood cells can pass; (iv) a first chamber in fluid communication with the conduit via the first filter, wherein the first chamber includes at least one electrode; and (v) a second chamber in fluid communication with the conduit via the second filter, wherein the second detection includes at least one electrode.

Some embodiments of the present disclosure provide a method including: (i) receiving, through a conduit, a volume of blood; (ii) receiving, into a first chamber, a portion of the volume of blood via a first filter, wherein the first chamber includes at least one electrode, and wherein the first filter includes a material that blocks passage of red blood cells; (iii) receiving, into a second chamber, a portion of the volume of blood via a second filter, wherein the second chamber includes at least one electrode, wherein the second filter includes a material that blocks passage of red blood cells, and wherein the second filter has at least one hole through which red blood cells can pass; (iv) detecting, using the at least one electrode of the first chamber, a first impedance of blood in the first chamber; (v) detecting, using the at least one electrode of the second chamber, a second impedance of blood in the second chamber; and (vi) determining, based on the first detected impedance and the second detected impedance, a hematocrit of the volume of blood received into the conduit.

Some embodiments of the present disclosure provide a system including: (i) a conduit; (ii) a first filter in fluid communication with the conduit, wherein the first filter includes a material that blocks passage of red blood cells; (iii) a second filter in fluid communication with the conduit, wherein the second filter includes a material that blocks passage of red blood cells, wherein the second filter has at least one hole through which red blood cells can pass; (iv) a first chamber in fluid communication with the conduit via the first filter, wherein the first chamber includes at least one electrode; (v) a second chamber in fluid communication with the conduit via the second filter, wherein the second chamber includes at least one electrode; (vi) a needle; (vii) an injector, wherein the injector is operable to drive the needle into skin to form a puncture in the skin and subsequently to retract the needle from the skin; (viii) a suction source; and (ix) a seal, wherein the injector drives the needle through the seal to form at least one hole in the seal, and wherein the suction provided by the suction source draws the volume of blood from the formed puncture in the skin into the conduit through the formed at least one hole in the seal.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7 is a block diagram of an example system that includes a plurality of wearable devices in communication with a server.

DETAILED DESCRIPTION

Figure 1A:
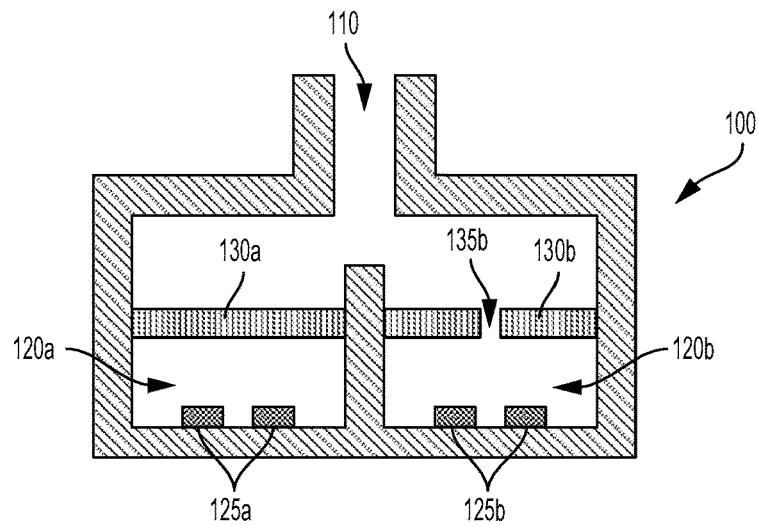
FIG. 1A is a cross-sectional view of an example sensor.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of a device to measure a hematocrit of blood, or to measure a volume percent of some particulate in some other fluid of interest, is desired.

I. OVERVIEW

It can be beneficial in a variety of applications to measure the cell content of a sample of blood, e.g., to diagnose a disease state, to control a dose of a drug to inform a treatment, or to facilitate some other action. Measuring the cell content of a blood sample can include measuring the hematocrit, or volume percent of red blood cells, of the sample. A hematocrit sensor is provided herein that can have a small size and that can detect the hematocrit of small samples of blood (e.g., blood samples having volumes less than 3 microliters). Hematocrit sensors as described herein can be incorporated into wearable devices or other small devices that can be used in a person's home, during activities of daily living, or in other situations or locations to facilitate frequent (e.g., once or more per day) measurement of the hematocrit of a person's blood without requiring the person to travel to a physician's office, hospital, or medical lab.

Hematocrit sensors as described herein include first and second chambers. The chambers are in fluid communication, via respective filters, with a blood input conduit through which a blood sample can be introduced into the sensor. Such a conduit could include channels, pipes, tubes, chambers (e.g., blood storage chambers), valves, one-way valves, hydrophobic and/or hydrophilic materials or coatings, capillary channels, branches, or other structures into which blood can be received and through which blood can be transported to the chambers and/or the filters. One of the filters blocks the passage of red blood cells while permitting the passage of other components of blood (e.g., plasma) while the other filter has at least one hole to permit the passage of red blood cells. Thus, one of the chambers can be filled with a portion of whole blood from a blood sample while the other chamber can be filled with a portion of the blood sample that is essentially free of red blood cells. Electrodes in the chambers can then be operated to measure the electrical impedance of each of the portions of the blood sample and the hematocrit of the blood sample can be determined from the measured impedances.

Blood could be provided into such a sensor by a variety of means. In some examples, a pump or other pressure source (e.g., blood pressure from a vein or artery from which the sample is taken) could be used to inject blood of a blood sample into the conduit of such a sensor. In another example, a source of suction (e.g., a pump, an evacuated volume) could be used to draw blood into the chambers via the conduit. In yet another example, hydrophilic materials could be disposed within the chambers to draw blood from a blood sample into the chambers.

A hematocrit sensor as described herein could be incorporated into a variety of devices. For example, such a hematocrit sensor could be configured to receive a blood sample from another device (e.g., from a sample container, from an IV line) and/or from a drop of blood that is already present on the skin of a person (e.g., due to the use of a lancet or other means for causing the expression of blood onto the skin surface). Additionally or alternatively, such a hematocrit sensor could be incorporated into a device or system that also includes a syringe, lancet, needle or other means for accessing blood from skin or other tissues of a person. Such a device could be a wearable device configured to facilitate automatic detection of the hematocrit of a person (e.g., at one or more specified times each day) by maintaining one or more hematocrit sensors and/or means for accessing blood from skin of a person (e.g., one or more injectors or lancets) in proximity to skin of the person.

As used herein, the term 'fluid communication' is used to describe a relationship between two or more chambers or other regions or objects that can contain and/or transport fluid (e.g., water, blood). Fluid may flow between two (or more) chambers, conduits, filters, or other objects or regions that are in fluid communication via laminar flow, turbulent flow, wicking, or some other fluid flow process. Fluid may flow in one direction (e.g., due to the presence of an interposed one-way valve) and/or both directions between first and second objects or regions that are in fluid communication.

It should be understood that the above embodiments, and other embodiments described herein, are provided for explanatory purposes, and are not intended to be limiting. Further, the terms 'access,' 'accessed,' 'accessing,' and any related terms used in relation to the operation of a hematocrit sensor of other device to induce emission of blood from skin are used herein (unless otherwise specified) to describe any operation or configuration of a device or system to receive blood from skin or from some other tissue. This could include receiving blood that has been emitted from skin in response to cutting, piercing, incising, cutting, or otherwise penetrating the skin. This could include actively pulling, wicking, suctioning, or otherwise drawing such emitted blood from the skin and/or form the surface of the skin into a hematocrit sensor and/or toward some other sensor, storage element, or other element(s) of a device. Further, while examples and embodiments described herein refer to accessing blood from skin, it should be understood that methods, hematocrit sensors, devices, and other embodiments described herein could be employed to access blood or other fluids from other environments of interest, e.g., from a sample container, an artery or vein, a dialysis machine, a heart-lung machine, or some other device or system.

II. EXAMPLE DEVICES TO DETECT HEMATOCRIT OF A BLOOD SAMPLE

The disclosed embodiments facilitate detection of hematocrit of a blood sample. These embodiments can beneficially detect the hematocrit of a blood using a small-volume blood sample (e.g., less than approximately 3 microliters) using a sensor that may have a small size (e.g., a volume less than a few cubic centimeters). These embodiments measure the hematocrit of a blood sample by detecting the impedance of a whole-blood portion of a blood sample, detecting the impedance of a portion of the blood sample that is essentially free of red blood cells due to filtration (e.g., plasma), and determining the hematocrit based on the two detected impedances. For example, the hematocrit of the blood sample can be determined based on a ratio of the detected impedances.

The two portions of a blood sample (one portion being whole blood and the other portion being blood that is essentially free of red blood cells) could be generated for the impedance measurement in a variety of ways. In some examples, portions of a blood sample could be provided into first and second chambers and electrodes within each of the chambers could be used, once the chambers have been filled with respective portions of a volume of blood, to determine the impedance of blood within each of the chambers. Blood could be provided to a first chamber via a first filter that blocks the passage of red blood cells while allowing the passage of plasma or other contents of blood such that the first chamber is filled with a portion of red-blood-cell-free blood. Blood could be provided to the second chamber via a second filter that is composed of a similar material to the first filter but that includes one or more holes to allow the passage of red blood cells such that the second chamber is filled with a portion of whole blood (that is, with a portion of blood that has a similar red blood cell content to the volume of blood from which the chambers receive their respective portions of blood). The second filter could be provided such that differences between impedances measured by electrodes of the first and second chambers correspond more to differences in the impedances of whole blood and red-blood-cell-free blood than to differences in the geometry and composition of the two chambers.

This configuration is illustrated by example in FIG. 1A. FIG. 1A shows an example hematocrit sensor 100 that includes first 120a and second 120b chambers. The chambers 120a, 120b are in fluid communication with a conduit 110 via first 130a and second 130b filters. The conduit 110 could include channels, pipes, tubes, chambers (e.g., blood storage chambers), valves, one-way valves, hydrophobic and/or hydrophilic materials or coatings, capillary channels, branches, or other structures into which blood can be received and through which blood can be transported to the chambers 120a, 120b and/or the filters 130a, 130b. The filters 130a, 130b are composed of a material that blocks passage of red blood cells while permitting passage of other components of blood. The second filter 130b has at least one hole 135b through which red blood cells can pass. The first chamber 120a includes a set of at least two electrodes 125a and the second chamber 120b includes a set of at least two electrodes 125b. The sets of electrodes 125a, 125b can be used to detect an impedance of blood (or other fluids) present in the first 120a and second 120b chambers, respectively, or to otherwise interact with fluids present in the chambers 120a, 120b (e.g., to determine an interface impedance between an electrode and a fluid, to determine an electrode potential of an electrode in a fluid, to determine a potentiometric voltage between two or more electrodes in a fluid).

Figure 1B:
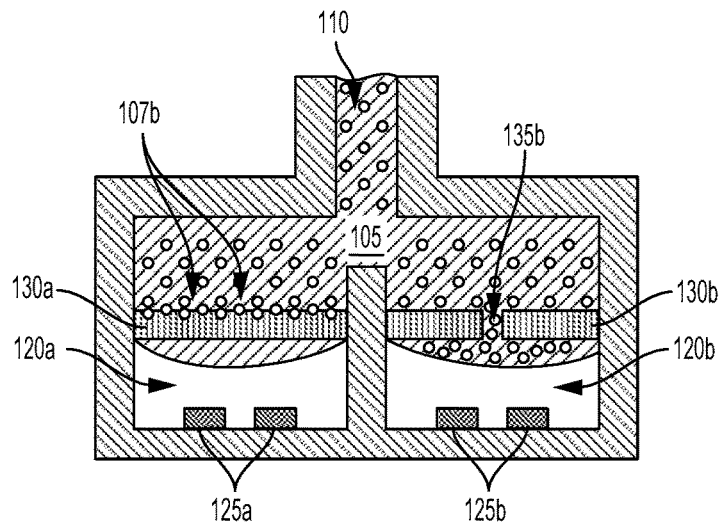
FIG. 1B is a cross-sectional view of the example sensor of FIG. 1A.

A volume of blood could be received into the conduit 110 and then enter the chambers 120a, 120b. This is depicted in FIG. 1B. A volume of blood 105 has entered the conduit 110 and portions of the volume of blood 105 are being received into the chambers 120a, 120b. Red blood cells are able to enter the second chamber 120b via the at least one hole 135b in the second filter 130a. The volume of blood 105 can be received into the conduit 110 and/or portion of the volume of blood 105 can be received into the chambers 120a, 120b by a variety of active and/or passive means, e.g., by pumping, by application of suction, by application of positive pressure, by wicking or capillary action, by disposing hydrophobic and/or hydrophilic materials or coatings within the sensor 100, or by some other means.

Figure 1C:
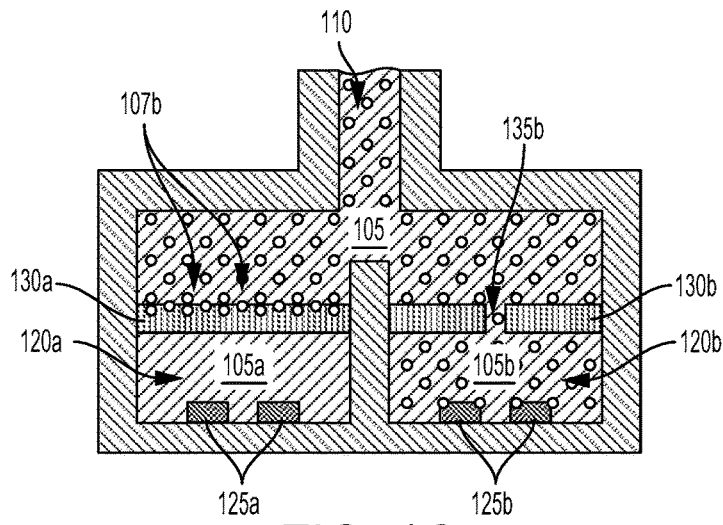
FIG. 1C is a cross-sectional view of the example sensor of FIGS. 1A and 1B.

Red blood cells are being stopped by the first filter 130a (illustrated by the absorbed red blood cells 107b disposed within a superficial volume of the first filter 130a) such that a portion of the volume of blood 105 that does not include red blood cells is being received into the first chamber 120a. FIG. 1C shows the hematocrit sensor 100 when both of the chambers 120a, 120b have been filled with respective portions of the volume of blood 105. The first chamber 120a has received a first portion of blood 105a that does not include red blood cells (e.g., that includes substantially only plasma or other non-cellular components of blood) while the second chamber 120b has received a second portion of blood 105b that includes red blood cells (e.g., that includes red blood cells to approximately the same degree as the received volume of blood 105). Impedances of the first 105a and second 105b received portions of blood can be detected using first 125a and second 125b sets of electrodes, respectively, and the detected impedances can be used to determine a hematocrit of the received volume of blood 105.

Figure 1D:
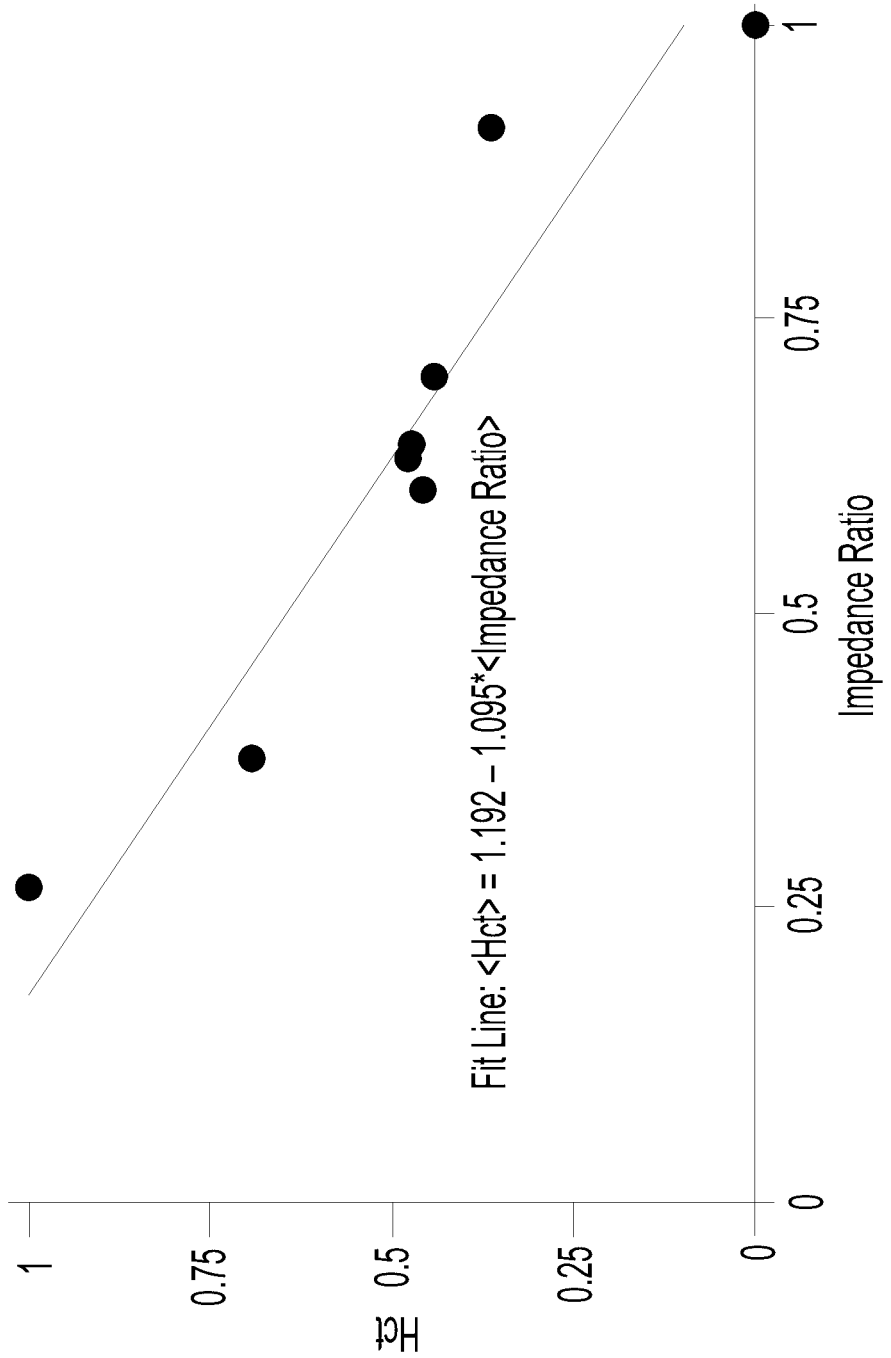
FIG. 1D is a graph of experimental results of the relationship between hematocrit of a blood sample and measured impedances of portions of the blood sample.

The hematocrit could be determined, based on the detected impedances of the portions of blood 105a, 105b in the chambers 120a, 120b, in a variety of ways. In some examples, a lookup table could be used to determine a hematocrit value based on discretized values of the detected impedances. The parameters of such a lookup table could be determined experimentally (e.g., by exposing a plurality of hematocrit sensors 100 to samples of blood having different hematocrits) or using a model of the relationship between whole blood impedance, cell-free blood impedance, and hematocrit. A ratio or other function could be used to determine a hematocrit value based on detected impedances. FIG. 1D shows an experimentally-measured relationship between hematocrit of a blood sample and the ratio of the detected whole-blood impedance of the sample and the detected cell-free blood impedance of the sample, detected using a hematocrit sensor as described herein. The hematocrit sensor used had chambers that were substantially similar in size, geometry, and composition.

As shown in FIG. 1D, the relationship between hematocrit and the impedance ratio determined using chambers of substantially similar configuration is roughly linear and has a negative slope. The offset, slope, or other properties of a linear relationship between the impedance ratio and hematocrit, or parameters of some other relationship between hematocrit and impedances measured using a hematocrit sensor as described herein, could be measured experimentally and/or determined using a model of blood and/or of the hematocrit sensor. As shown in FIG. 1D, an experimentally determined, best-fit linear relationship between the hematocrit and the ratio of the detected impedances can be used to determine a hematocrit value, based on a determined impedance ratio, by subtracting the determined impedance ratio, scaled up by a factor of 1.095, from an offset hematocrit value of 1.192. In some examples, first and second chambers of a hematocrit sensor as described herein could differ with respect to size, geometry, configuration, or some other properties and the hematocrit of a blood sample could be determined based on a different linear (or other) relationship between hematocrit and the ratio of the impedances detected from different chambers of the hematocrit sensor.

The filters 130a, 130b could be composed of any materials that allow for the passage of plasma or other blood contents while blocking the passage of red blood cells. For example the filters could include materials formed into a mesh, fabric, or other structure to prevent the passage of red blood cells or other large solid or semi-solid contents of the blood while permitting passage of other contents of the blood (e.g., plasma). The filters could be formed from a hydrophilic material and/or a material that includes a hydrophilic coating in order to draw blood contents into and/or through the filters. In one example, the filters 130a, 130b could be composed of foamed polysulfone. The filters 130a 130b and/or other components of the sensor 100 (e.g., the walls of the conduit 110) could be coated with and/or contain substances to prevent coagulation or clotting of blood. Note that, while hematocrit sensors herein are described as including two (or more) filters, such filters may be formed from a single element of filter material. For example, a single element of filter material could be disposed within a sensor housing that includes first and second chambers such that different areas or volumes of the single element of filter material comprise different (e.g., first and second) filters through which the first and second chambers, respectively, may receive portions of a blood sample.

The sets of electrodes 125a, 125b could have a geometry and/or composition specified to facilitate their use in determining the impedance of fluid samples (e.g., portions of a volume of blood received through the conduit 110). Such detection could include applying an alternating current through and/or voltage between the electrodes and measuring a resulting voltage between/current through the electrodes. The frequency, amplitude, and/or waveform of such an alternating current/voltage could be specified to prevent damaging the electrodes, to prevent electrode polarization, to generate a resulting voltage/current having a desired amplitude, or according to some other consideration. For example, an alternating current having an amplitude of approximately 600 microamps and a frequency of approximately 15 kHz could be applied through a set of electrodes having areas of at least 0.5 square millimeters each to generate a resulting alternating voltage between the electrodes having an amplitude of a few volts, e.g., having an amplitude that is less than the electrolysis voltage of water (approximately 1.23 volts). Further, the area, geometry, composition, or other properties of the electrodes could be specified to facilitate impedance measurement or according to some other consideration. For example, the electrodes 125a, 125b could be composed of gold (e.g., gold-plated printed circuit board traces), silver, silver chloride, platinum, or some other metal(s) and could have areas greater than approximately 0.5 square millimeters (e.g., to prevent electrolysis of water by distributing applied alternating currents across the area of the electrodes). Additionally or alternatively, smaller alternating currents could be applied through smaller-area electrodes.

Note that, while chambers as illustrated herein each include at least two electrodes for the detection of impedances of blood or other fluids within the chambers, a chamber of a hematocrit sensor as described herein could include more or fewer electrodes. For example, a chamber could include a single electrode that could be used, in combination with another electrode located outside of the chamber and in electrical contact with a blood sample received into the sensor, to detect the impedance of fluid in the chamber. For example, such a counter electrode could be disposed within a conduit (e.g., 110) of the hematocrit sensor. In some examples, such a counter electrode could be shared between multiple chambers of a hematocrit sensor to facilitate detection of impedances of fluids in each of the multiple chambers.

To facilitate measurement of the impedance of portions of a received blood sample and/or to facilitate other functions of a hematocrit sensor as described herein, a hematocrit sensor could include substances to prevent coagulation, clotting, or other processes that may occur in a sample of blood. Such substances could include anticoagulants, antiplatelet drugs, thrombolytic drugs, or other substances. For example, an amount of heparin could be provided in one or more aspects of the hematocrit sensor 100 that may come into contact with a portion of a blood sample. Such substances could be provided, e.g., within and/or on a surface of the conduit 110, the first chamber 120a, the second chamber 120b, the first filter 130a, the second filter 130b, or some other aspect of the hematocrit sensor 100 that may come into contact with a portion of a blood sample received into the hematocrit sensor 100.

A device that includes the hematocrit sensor 100 could include multiple different sensors configured to measure other properties of a blood sample. For example, such a device could include analyte sensors (e.g., electrodes made selectively sensitive to a specified analyte by disposing an analyte-sensitive substance on one or more of the electrodes), light emitters, light detectors (e.g., to detect an oxygenation state of the blood, to detect a fluorescent substance in the blood), viscosimeters, or other sensors configured to detect one or more properties of blood. Further, such a device could include means for detecting such properties of multiple different samples of blood. For example, a device could include multiple instances of the hematocrit sensor 100 and could apply different blood samples (e.g., blood samples accessed at respective different points in time) to respective different hematocrit sensors or other sensors.

A volume of blood could be received into a blood input conduit of a hematocrit sensor via a variety of passive and/or active processes. In some examples, pressure could be applied from outside to drive a volume of blood into the conduit. Such pressure could be provided by a pump, by blood pressure in a vein or artery from which the blood sample is being received, or from some other source. Additionally or alternatively, the hematocrit sensor could include means for drawing blood into the conduit and/or into chambers of the sensor. This could include drawing the blood from a drop that is present on the surface of skin (e.g., due to a lancet inducing an incision in the skin), from within a puncture in skin created by a needle or other device (e.g., a needle propelled into the skin by a device that also includes the hematocrit sensor), from a sample container, or from some other source.

Figure 2A:
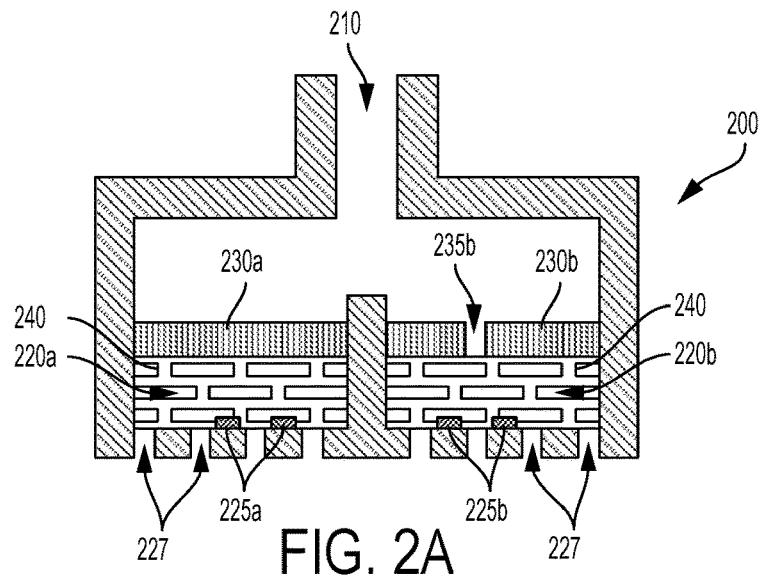
FIG. 2A is a cross-sectional view of an example sensor.

In some examples, hydrophilic and/or hydrophobic materials could be used to draw a blood sample into the sensor and/or a geometry of one or more components of the sensor could be specified to draw the blood into the sensor using capillary forces. For example, a mesh or otherwise formed hydrophilic material could be disposed within the chambers of a hematocrit sensor to draw portions of a volume of blood into the chambers. This is illustrated by way of example in FIGS. 2A-C. FIG. 2A shows an example hematocrit sensor 200 that includes first 220a and second 220b chambers. The chambers 220a, 220b are in fluid communication with a conduit 210 via first 230a and second 230b filters. The filters 230a, 230b are composed of a material that blocks passage of red blood cells while permitting passage of other components of blood. The second filter 230b has at least one hole 235b through which red blood cells can pass. The first chamber 220a includes a set of at least two electrodes 225a and the second chamber 220b includes a set of at least two electrodes 225*b*. A hydrophilic material 240 is disposed within the first 220*a* and second 220*b* chambers. The hydrophilic material 240 can provide a capillary or other force(s) to draw portions of a blood sample into each of the chambers 220*a*, 220*b* via the conduit 210. The chambers 220*a*, 220*b* also include vents 227 to allow air or other gas that is present in the chambers 220*a*, 220*b* to be displaced from the chambers 220*a*, 220*b* by portions of blood that are received into the chambers 220*a*, 220*b*. Such vents 227 could also be used to apply suction to draw blood into the chambers 220*a*, 220*b*.

Figure 2B:
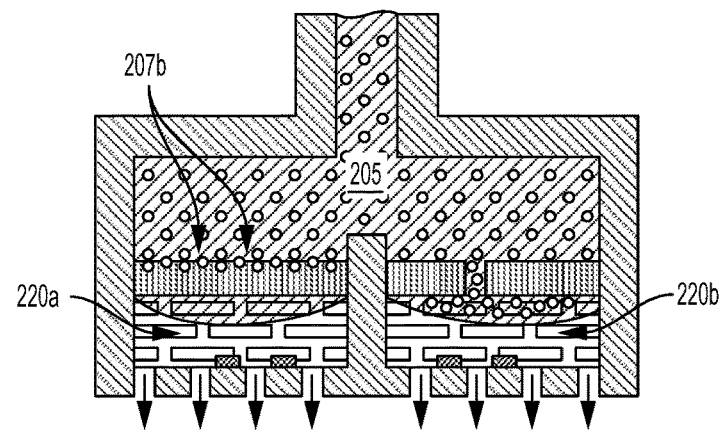
FIG. 2B is a cross-sectional view of the example sensor of FIG. 2A.

This is depicted in FIG. 2B. A volume of blood 205 has entered the conduit 210 and portions of the volume of blood 205 are being drawn into the chambers 220*a*, 220*b* by the hydrophilic material 240. Red blood cells are able to enter the second chamber 220*b* via the at least one hole 235*b* in the second filter 230*a*. Red blood cells are being stopped by the first filter 230*a* (illustrated by the absorbed red blood cells 207*b* disposed within a superficial volume of the first filter 230*a*) such that a portion of the volume of blood 205 that does not include red blood cells is being received into the first chamber 220*a*. As the chambers 220*a*, 220*b* receive portions of blood, air is displaced out of the chambers 220*a*, 220*b* via the vents 227 (illustrated by arrows).

Figure 2C:
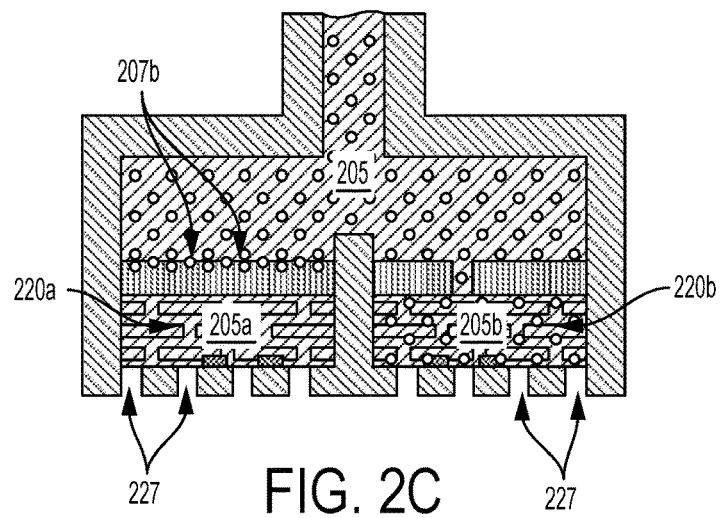
FIG. 2C is a cross-sectional view of the example sensor of FIGS. 2A and 2B.

FIG. 2C shows the hematocrit sensor 200 when both of the chambers 220*a*, 220*b* have been filled with respective portions of the volume of blood 205. The first chamber 220*a* has received a first portion of blood 205*a* that does not include red blood cells (e.g., that includes substantially only plasma or other non-cellular components of blood) while the second chamber 220*b* has received a second portion of blood 205*b* that includes red blood cells (e.g., that includes red blood cells to approximately the same degree as the received volume of blood 205). Impedances of the first 205*a* and second 205*b* received portions of blood can be detected using first 225*a* and second 225*b* sets of electrodes, respectively, and the detected impedances can be used to determine a hematocrit of the received volume of blood 205.

The hydrophilic material 240 could include a variety of different material compositions and/or coatings disposed as a mesh, a fabric, a foam, a plurality of microbeads, fibers, or other particles, or disposed in some other way such that the hydrophilic material 240 can draw portions of blood into the chambers 220*a*, 220*b* while allowing red blood cells to enter the second chamber 220*b*. For example, the hydrophilic material 240 in each chamber 220*a*, 220*b* could include one or more discs of a hydrophilic mesh. The hydrophilic material 240 could include a base material (e.g., a polymer) onto which a hydrophilic or super-hydrophilic coating or material has been deposited or formed. Additionally or alternatively, a geometry, weave, or other geometric property of the hydrophilic material 240 could be specified to increase the ability of the hydrophilic material 240 to draw blood into the chambers 220*a*, 220*b*.

Additionally or alternatively, a hematocrit sensor could be configured to apply suction to draw blood into the sensor from a source of the blood (e.g., from a puncture in skin, from a drop of blood on the surface of skin, from a sample container, from an IV line, from a component of a dialysis machine) and/or to draw blood into a chamber (e.g., via a conduit). Such suction could be provided by a pump, by one or more evacuated volumes, or by some other suction source of the hematocrit sensor and/or of a device that includes the hematocrit sensor. In examples where suction is provided by one or more evacuated volumes, such volumes could include the chambers of the sensor. Further, such suction could be controllably applied to a blood source and/or the chambers by a valve, by puncturing a seal that separates the evacuated volumes from the ambient environment, or by some other means.

Figure 3A:
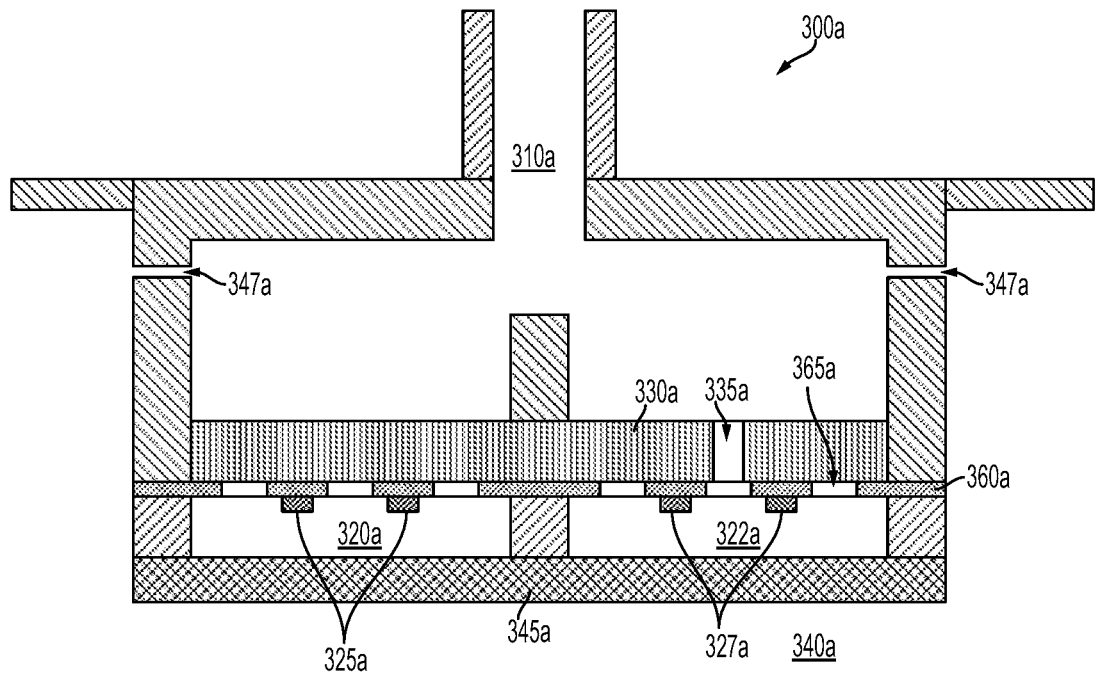
FIG. 3A is a cross-sectional view of an example sensor.

FIG. 3A shows an example hematocrit sensor 300*a* that includes first 320*a* and second 322*a* chambers. The chambers 320*a*, 322*a* are in fluid communication with a conduit 310*a* via first and second filters that are formed from a single element of filter material 330*a*. The filter material is configured to block passage of red blood cells while permitting passage of other components of blood. The second filter (that is, the portion of the element of filter material 330*a* through which the second chamber 322*a* can receive blood from the conduit 310*a*) has at least one hole 335*a* through which red blood cells can pass. The first chamber 320*a* includes a set of at least two electrodes 325*a* and the second chamber 322*a* includes a set of at least two electrodes 327*a*. The chambers 320*a*, 322*a* are exposed, via a gas-permeable membrane 345*a*, to suction (represented by a low-pressure region 340*a*).

The suction could be provided by a pump. Additionally or alternatively, the suction could be provided by an evacuated volume. In some examples, the evacuated volume could include the chambers 320*a*, 322*a*. For example, the chambers 320*a*, 322*a* could be evacuated and then coupled to a sample of blood (e.g., by opening a valve or by breaching a seal that separates the evacuated volume from the ambient environment and/or the blood sample) such that the evacuated volume provides suction to draw portions of a volume of blood into the chambers 320*a*, 322*a* via the conduit 310*a*. A portion of such suction could be provided to the chambers 320*a*, 322*a* via the gas-permeable membrane 345*a*.

The gas-permeable membrane is configured to allow suction to be applied and/or gas to pass through the membrane 345*a* while preventing the passage of blood plasma (that is, the gas-permeable membrane 345*a* is impermeable to blood plasma). The gas-permeable membrane 345*a* could be composed of a variety of materials and/or surface coatings configured in a variety of ways (e.g., as a woven fabric, as a mesh of polymer fibers). For example, the gas-permeable membrane 345*a* could be composed of a porous mesh or fabric composed of hydrophobic materials and/or materials coated with hydrophobic substances. In some examples, the gas-permeable membrane 345*a* could be composed of expanded polytetrafluoroethylene (ePTFE).

Note that, while gas-permeable membranes as described herein may be illustrated as including two (or more) gas-permeable membranes, such membranes may be formed from a single element of gas-permeable material, as shown in FIG. 3A. As shown in FIG. 3A, a single element of gas-permeable material could be disposed within a sensor housing that includes first and second chambers such that different areas or volumes of the single element of gas-permeable material comprise different (e.g., first and second) gas-permeable membranes through which the first and second chambers, respectively, may be provided suction.

The hematocrit sensor 300*a* includes vacuum bypass ports 347*a*. These ports 347*a* couple the volume of the conduit 310*a* to the suction source (e.g., to an evacuated volume comprising the low-pressure region 340*a*). These ports 347*a* could be provided to allow a suction source to continue applying suction to a source of blood after the chambers 320*a*, 322*a* have been filled. Such suction could be provided to remove blood from a skin surface, to access an additional volume of blood (e.g., to provide to further sensors and/or to store for later analysis), or to facilitate some other application. The size (e.g., length, diameter) of the ports 347*a* could be specified such that a suction source (e.g., an evacuated volume) can apply sufficient suction, via the chambers 320*a*, 322*a*, to fill the chambers 320*a*, 322*a*.

Figure 3B:
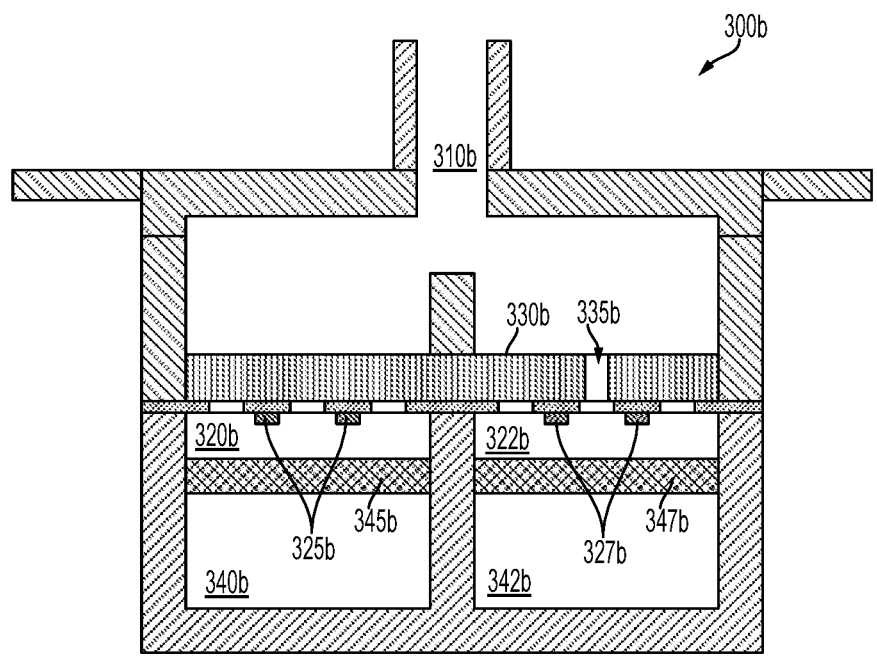
FIG. 3B is a cross-sectional view of an example sensor.

Each chamber of a hematocrit sensor could receive suction from a respective suction source, e.g., to tailor an amount of suction, a suction profile over time, a maximum suction, or some other property of suction applied to the chambers. FIG. 3B shows an example hematocrit sensor 300*b* that includes first 320*b* and second 322*b* chambers. The chambers 320*b*, 322*b* are in fluid communication with a conduit 310*b* via first and second filters that are formed from a single element of filter material 330*b*. The filter material is configured to block passage of red blood cells while permitting passage of other components of blood. The second filter (that is, the portion of the element of filter material 330*b* through which the second chamber 322*b* can receive blood from the conduit 310*b*) has at least one hole 335*b* through which red blood cells can pass. The first chamber 320*b* includes a set of at least two electrodes 325*b* and the second chamber 322*b* includes a set of at least two electrodes 327*b*. The chambers 320*b*, 322*b* are exposed, via first 345*b* and second 347*b* gas-permeable membranes, respectively, to suction provided at least in part by first 340*b* and second 342*b* evacuated volumes. The evacuated volumes 340*b*, 342*b* could have respective sizes, geometries, or other properties such that the suction provided to each of the chambers 320*b*, 322*b* is different.

A hematocrit sensor as described herein could include multiple different means for causing a sample of blood to be received into the sensor and/or for portions of the blood sample to be received into chambers of the sensor. For example, a hematocrit sensor may include evacuated volumes or other suction sources to provide suction to draw portions of blood into chambers of the sensor and the chambers could include elements of a hydrophilic material. A chamber of a hematocrit sensor could include vents to allow air or other gases (e.g., a low-density gas present in an evacuated volume, e.g., in an evacuated chamber) to be displaced out of the chamber by blood that is drawn into the chamber by applied suction and/or by some other means.

In some examples, a hematocrit sensor includes an evacuated volume that acts as a suction source to draw blood from an environment (e.g., from on or within skin) into chambers of the sensor via a blood input conduit. In such examples, the evacuated volume could be separated from the environment (e.g., from skin and/or blood) by a seal. Further, the chambers could form part of the evacuated volume. The seal could be broken by a needle driven through the seal to form one or more holes through which suction may be applied, by the evacuated volume, to draw blood through the formed one or more holes into the hematocrit sensor and/or into other sensors, blood storage elements, or other elements of such a device. The needle used to puncture the seal could also be configured to penetrate skin, forming a puncture through which blood may be drawn from the skin. A needle or other penetrating means of such a device could be configured to be driven into the skin by injecting means (e.g., by a piston and a chemical propellant) and subsequently retracted from the skin (e.g., by a spring) such that blood can be emitted from the resultant wound (e.g., puncture) in the skin and drawn, by an applied suction, into the device and further into chambers of a hematocrit sensor of such a device.

Such blood-accessing and/or hematocrit-detecting devices could be configured to access, detect, store, or otherwise interact with blood in a variety of ways. In some examples, such devices could be configured to be mounted to skin or otherwise worn such that the device can access blood automatically, e.g., a controller or other element(s) of the device could operate an injector of the device to pierce the skin, access blood, and measure the hematocrit of the blood while a wearer of the device sleeps. Alternatively, the device could be a handheld device configured to be manually mounted to a portion of skin and operated to access blood from the skin. In some examples, the device could be wall-mounted, situated on a desktop, or disposed or mounted in some other way, and mounting the device to skin could include positioning an arm or other aspect of a body proximate to the device (e.g., positioning skin of the wrist of a person proximate to a specified aspect of the device). In some examples, one or more elements (e.g., injectors, needles, seals, suction sources, hematocrit sensors, blood storage elements) could be removable from the device, e.g., such that other elements of the device (e.g., controllers, user interfaces, mounts) could be reusable by replacing used removable elements of the device.

The volume of blood received from skin by such a device can be related to the configuration of the device, and could be between approximately one and approximately 10 microliters. For example, the device could be configured to access (e.g., to penetrate the skin and to apply suction to the skin to draw) approximately 3 microliters or less of blood and to detect the hematocrit of the accessed blood. The device could be configured (e.g., a stroke length, diameter or shape of a needle, the shape of a concave depression into which skin could be drawn by suction, an amount of applied suction) to provide a specified minimum amount of blood according to a property of the blood to be measured and/or a sensor used to detect such a property.

Figure 4A:
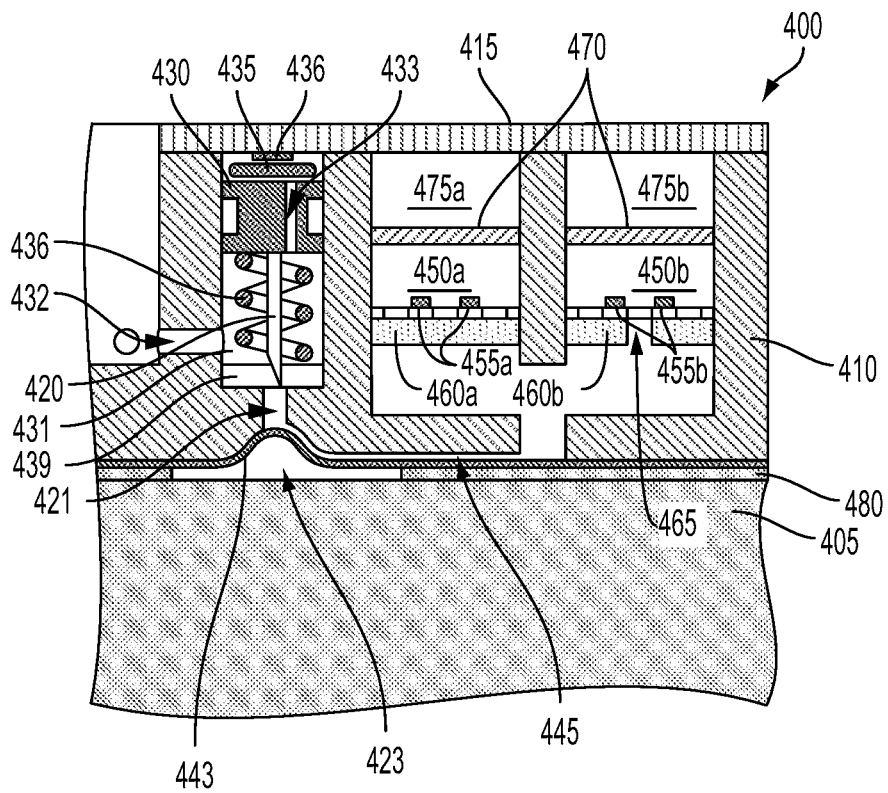
FIG. 4A is a cross-sectional view of an example device mounted to a skin surface.

FIGS. 4A-D illustrate the operation of an example of such a device to access blood from skin and to detect the hematocrit of the accessed blood. FIG. 4A shows the device 400 having been mounted to the skin 405; this could include the device 400 being adhered to the skin 405 using an adhesive or mount (e.g., a mount configured to encircle a wrist of a person such that the device 400 is maintained in contact with skin of the wrist). Alternatively, the device 400 could be a handheld device designed to be manually or otherwise maintained in contact with the skin 405. In another example, the device 400 could be a desktop or other relatively immobile device and a body part comprising the skin 405 could be positioned proximate the device 400 as illustrated.

The device 400 includes a housing 410 that is formed to include one or more injector chambers 431, chambers 450*a*, 450*b*, conduits 445, and evacuated volumes 475*a*, 475*b* as well as other features. The chambers 450*a*, 450*b*, evacuated volumes 475*a*, 475*b*, and conduit 445 form a single evacuated volume contained by a seal 443. The device 400 could be used on its own (e.g., by placing a bottom surface of the device 400 in contact with skin), could be part of another device (e.g., part of a wrist-mountable or otherwise body-mountable device), could be a removable module of another device, or could be configured or operated in some other way.

The device 400 includes a hematocrit sensor as described herein. The hematocrit sensor includes the chambers 450*a*, 450*b*, the conduit 445, first 460*a* and second 460*b* filters via which the chambers 450*a*, 450*b* can receive blood from the conduit 445, one or more electrodes 455*a*, 455*b* disposed in each of the chambers 450*a*, 450*b* for detecting the impedance of fluid in the chambers 450*a*, 450*b*, and other elements. The hematocrit sensor further includes gas-permeable membranes 470 through which the evacuated volumes 475*a*, 475*b* can provide suction to the chambers 450*a*, 450*b*, respectively, to draw blood into the chambers, from the conduit 445 via the first 460a and second 460b filters, respectively. The filters 460a, 460b are composed of a material that prevents the passage of red blood cells while allowing the passage of other components of blood (e.g., plasma). The second filter 460b has one or more holes 465 through which red blood cells can move.

The injector chamber 431 can be a cylindrical shape formed in the housing 410, but could assume other shapes according to an application. The chamber contains a needle 420 configured to penetrate skin, a piston 430 coupled to the needle 420 and configured to slidably move within the chamber 431 (e.g., along the long axis of the chamber 431), and a propellant 435 configured to slidably move the piston 430 within the chamber 431 to drive the needle 420 into skin and further to drive the needle 420 through the seal 443 disposed on a bottom surface of the housing. The chamber additionally contains a spring 437 configured to retract the needle 420 from the skin, a sealant layer 439 that is configured to be pierced by the needle 420 and a resistive element 436 configured to ignite the propellant 435 by providing sufficient heat to the propellant 435 when current passes through the resistive element 436.

The top of the chamber 431 is closed by a circuit board 415 or other member bonded or otherwise adhered to the housing 410. Electronics 450 (e.g., one or more processors, logic gates, current sources, electronic switches, radio transceivers, analog-to-digital converters) disposed on the circuit board 415 could be configured to perform operations of the device 400, e.g., to apply current to the resistive element 436 (or to other resistive elements or to operate other components of other injectors of the device 400) to ignite the propellant 435 at a specified point in time, to apply an alternating current through electrodes 455a, 455b of the device 400 to detect an impedance of one or more portions of blood accessed by the device (e.g., to facilitate determination of the hematocrit of the accessed blood), or to perform some other operations according to an application.

A needle channel 421 is formed in the bottom of the chamber 431 through the housing 410 such that the needle 420 can be driven into skin proximate the bottom of the housing 410. A piston vent 433 is formed through the piston 430 and chamber vents 432 are formed in the housing 410 to allow gases produced by the ignition of the propellant 435 to be vented out of the device such that the spring 437 can retract the needle 420 subsequent to the ignited propellant 463 causing the piston 430 to drive the needle 420 through the seal 443 and into skin. The diameter, number, geometry, and other properties of the vents 433, 432 could be specified to control a force with which the piston 430 drives the needle 420, a duration of time during which the needle 420 penetrates skin before being retracted by the spring 437, or other properties of operation of the device 400.

The seal 443 includes a concave depression 423 through which the needle 420 penetrates the seal 443 to form a hole in the seal 443 when driven downward by the piston 430. A channel that forms part of the conduit 445 is formed above the concave depression 423 behind the seal 443 and connecting the region behind the seal 443 with an evacuated volume formed in the housing 410. The evacuated volume includes the conduit 445, the chambers 450a, 450b, and the evacuated volumes 475a, 475b. The top of the evacuated volume is sealed by the circuit board 415. Atmospheric gases are prevented from entering the evacuated volume 443 through the injector chamber 431 by the sealant layer 439 and prevented from entering the evacuated volume through the bottom of the housing 410 (e.g., through the concave depression 423) by the seal 443.

The pressure in the evacuated volume is sufficiently lower than the pressure of the environment surrounding the device 400 that, when one or more holes are formed in the seal 443 by the needle 420, the evacuated volume (e.g., the evacuated volumes 475a, 457b) acts as a suction source to draw blood from skin, through the one or more holes in the seal 443, through the conduit 445, through the filters 460a, 460b, and into the chambers 450a, 450b such that electrodes 455a, 455b in the chambers 450a, 450b can detect the impedance of portions of the received blood in each of the chambers 450a, 450b. Such detected impedances could be used to determine a hematocrit of the blood accessed form the skin 405. In such an example, the conduit 445 could additionally act as a collection chamber for blood. The evacuated volume could have a pressure less than approximately 50 kilopascals.

The device 400 additionally includes a conformal layer 480 configured to conform to the skin such that suction applied by the evacuated volume (or by some other suction source of the device 400) through one or more holes in the seal 443 is applied to skin proximate the one or more holes in the seal 443. The conformal layer 480 could include polyurethane, soft rubber, polymeric gel, or some other compliant material. Additionally or alternatively, the conformal layer 480 could include a glue (e.g., cyanoacrylate), a tape, a dry adhesive, or some other adhesive substance.

Figure 4B:
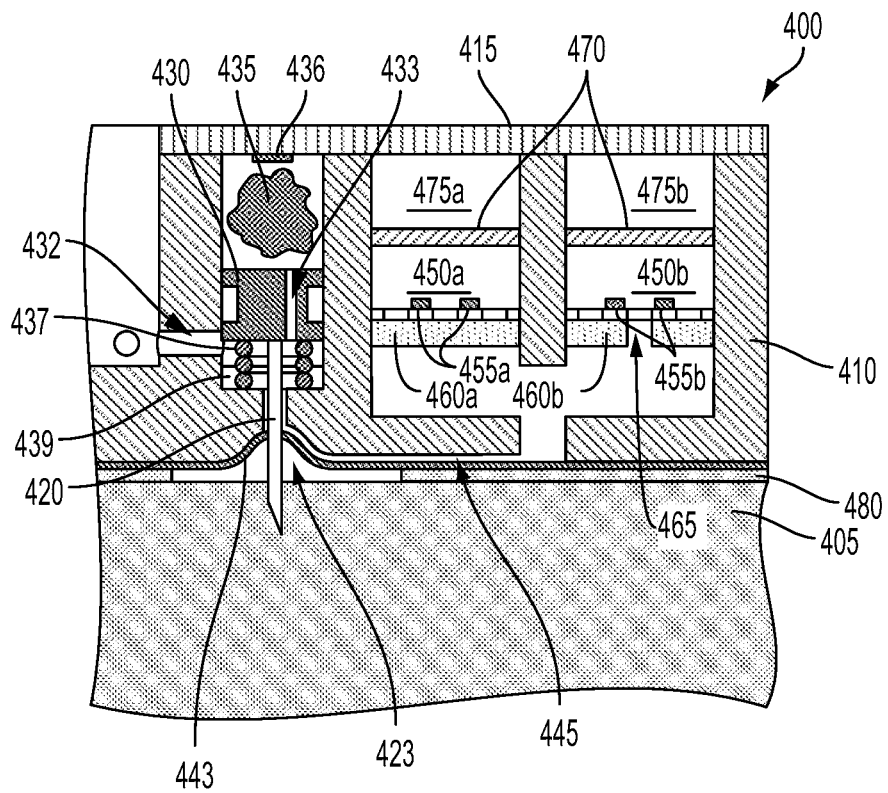
FIG. 4B is a cross-sectional view of the example device of FIG. 4A when a needle of the example device is piercing the skin.

FIG. 4B shows the propellant 435 expanding to slidably move the piston 430 downward, compressing the spring 437 and driving the needle 420 to pierce the seal 443 and further driving the needle 420 into the skin 405. Properties of the spring 437 (e.g., a spring constant, a degree of initial loading), piston 430 (e.g., a mass, a coefficient of friction with the sides of the chamber 431, a diameter and number of piston vents 433), needle 420 (e.g., a diameter, a tip geometry, the presence of a fluoropolymer coating or other anti-friction coating), injector chamber 431 (e.g., a geometry, a volume of the region above the piston), propellant 435 (e.g., an amount of the propellant, a mix of chemicals comprising the propellant), or other elements of the device 400 could be specified to maximize the speed with which the needle 420 is driven into the skin 405 to, e.g., reduce discomfort induced in a user by operation of the device to penetrate the skin 405.

Figure 4C:
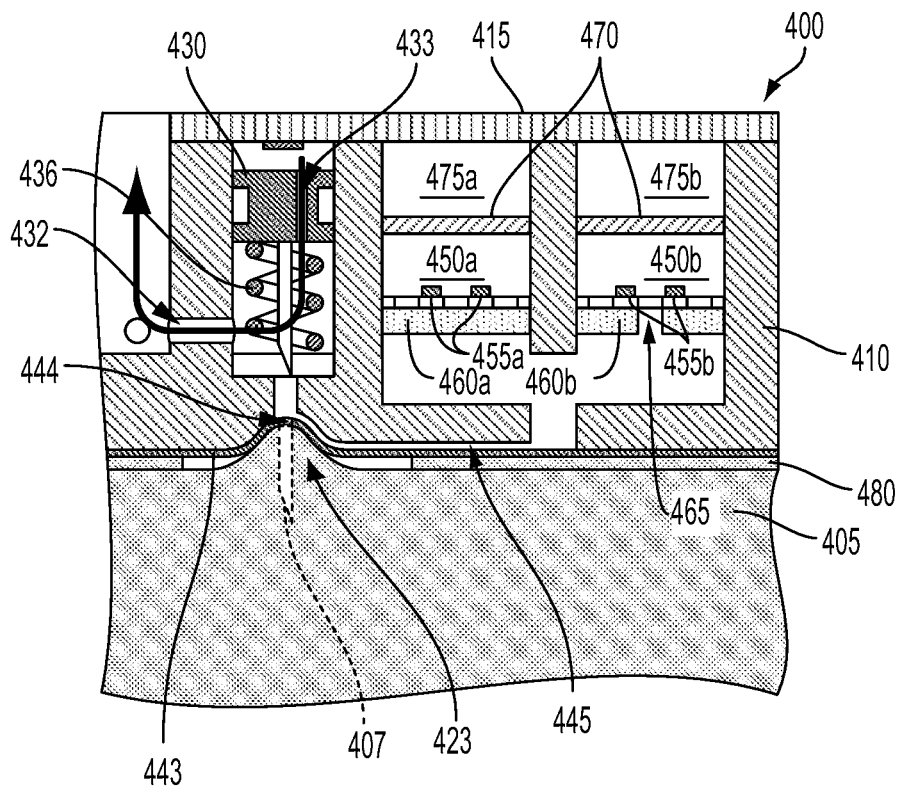
FIG. 4C is a cross-sectional view of the example device of FIG. 4B when the needle of the example device has retracted from the skin.

FIG. 4C shows the piston 430 and needle 420 retracted from the skin 405 partially due to venting of propellant gases through the piston vent 433 and chamber vents 432 (indicated by the arrow) and the force generated by the spring 437 due to compression of the spring 437 by the movement of the piston 430 downward when driving the needle 420 into the skin 405 (shown in FIG. 4B). FIG. 4C additionally shows a hole 444 formed in the seal 443 and a puncture 407 formed in the skin 405 by the piston 430 driving the needle 420 through the seal 443 and into the skin 405. The hole 444 in the seal 443 allows skin proximate the hole 444 (e.g., skin beneath the concave depression 423) to be exposed to suction from the evacuated volume. This causes the skin 405 proximate the hole 444 to be drawn up into the concave depression 423. Further, the skin 405 is drawn up into the concave depression 423 such that the puncture 407 is aligned with the hole 444. This could facilitate the drawing of blood from the skin 405 (e.g., from the puncture 407) through the hole 444 into the device 400. In examples where skin is drawn, by suction, toward a device such that a formed puncture in the skin is not aligned with one or more formed holes in a seal, blood could still be drawn into the device, e.g., due to wicking, surface tension, the blood filling the space between the skin and device, or by some other mechanism.

Properties of the spring 437, piston 430, needle 420, injector chamber 431, propellant 435, or other elements of the device 400 could be specified to maximize the speed with which the needle 420 is retracted from the skin 405 and/or minimize the duration during which the needle 420 pierces the skin 405 to, e.g., reduce discomfort induced in a user by operation of the device to penetrate the skin 405. Further, elements of the device 400 could be configured to minimize an amount of blood emitted from the skin 405 that is deposited on the surface of the skin 405 rather than being drawn and/or suctioned into the device 400 (e.g., the device 400 could be configured to suction the skin 405 into contact with the seal 443; the seal 443 could include a hydrophobic or other coating to repel blood).

Figure 4D:
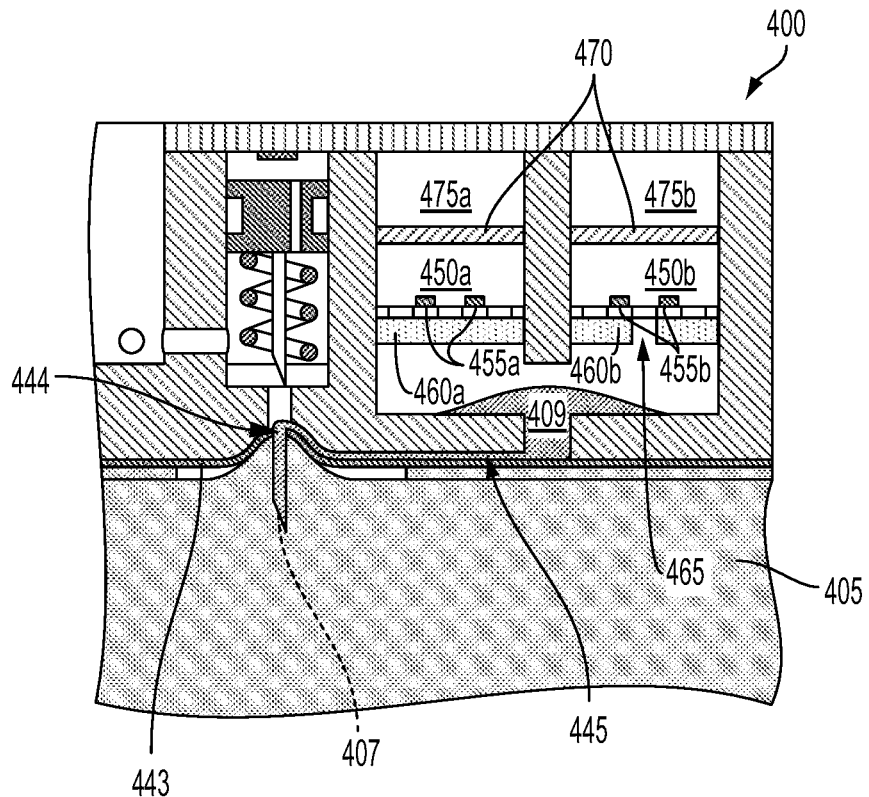
FIG. 4D is a cross-sectional view of the example device of FIG. 4C when blood from the skin has been suctioned to a sensor of the example device.

FIG. 4D shows blood 409 emitted from the skin 405 (e.g., from the puncture 407 formed in the skin 405) that has been drawn through the hole 444 and into the device 400. Further, the emitted blood 409 has been directed, via the conduit 445, to the chambers 450a, 450b of the hematocrit sensor. Suction from the evacuated volume could further draw portions of the blood 209 through the filters 460a, 460b into the chambers 450a, 450b. Additionally or alternatively, the blood 409 could be directed to and/or through the hole 444, through the conduit 445, and/or into the chambers 450a, 450b by hydrophobic and/or hydrophilic coatings or material on one or more surfaces of the seal 443, conduit 445, or other elements of the device 400. For example, a path from the hole 444 through the channel of the conduit 445 to the filters 460a, 460b could be coated with a hydrophilic substance; other surfaces of the device 400 that could come into contact with the blood 409 could be coated with a hydrophobic substance. Additionally or alternatively, the channel (or other elements of the device 400) could be sized to direct the blood 409 using capillary action. The channel or other elements of the device 400 could include a coating of heparin or some other pharmaceutical to reduce coagulation and/or clotting of the blood 409 in the device (e.g., to increase the duration and/or amount of blood 409 flowing into the device 400 and/or into the chambers 450a, 450b).

The shape, size, geometry, or other properties of the concave depression 423 could be specified to maximize an amount of blood emitted from the skin 405 in response to being pierced by the needle 420. For example, the concave depression 423 could have a conical shape. The device 400 could additionally or alternatively be configured in other ways to maximize an amount of blood emitted from the skin 405. For example, the device 400 could be configured to increase blood flow in the skin 409 proximate the device 400 and/or proximate the concave depression 423 by, e.g., heating the skin 405 before penetration, applying a frictive force to the skin before penetration (e.g., by rubbing the skin), applying suction to the skin 405 before penetration, applying a vasodilating, anti-clotting, anti-coagulant, or other pharmaceutical (e.g., heparin, lidocaine) before, during, and/or after penetration of the skin 405, or by being configured or operated in some other way. Pharmaceuticals could be delivered as a coating on the needle 420. Additionally or alternatively, the needle 420 could be hollow and used to deliver a pharmaceutical or other substance and/or to suction blood into the device 400 via such a hollow needle.

Further, the properties of the needle 420 could be specified to maximize the amount of blood emitted from the skin 405, minimize discomfort induced by penetration of the skin, or according to some other consideration. For example, the tip of the needle 420 could include a triple-bevel to minimize deflection of the skin 405 and/or to minimize induced discomfort due to piercing of the skin 405 by the needle 420. Alternatively, the needle 420 could have a chisel tip (e.g., a single bevel), could have a flat 'razor' blade end, could include a taper (e.g., could become thinner toward the end), could be round, flat, or could be configured in some other way to, e.g., maximize blood emitted from the skin 405. The needle 420 could be serrated. The diameter (or gauge) of the needle 420 could be specified to maximize the amount of blood emitted from the skin 405 and/or to minimize discomfort induced by piercing of the skin 405 by the needle 420. For example, the needle 420 could have a gauge between approximately 21 gauge and approximately 36 gauge. In some examples, the piston 430 could drive multiple needles into the skin.

The propellant 435 could include a variety of chemicals and combinations of chemicals. For example, the propellant 435 could include nitrocellulose, butane, azide, or some other energetic gas-producing substance or other chemical(s). In some examples, the propellant could be formed and/or modified before use, e.g., the propellant could include oxygen and hydrogen formed from water by electrolysis. Alternatively, the propellant could include a compressed gas (e.g., $CO_2$, $N_2$, air compressed by a pump or other means, a goas generated by the device 100 by electrolysis or some other method or means) to which the piston 430 is exposed to drive the needle 420 into the skin 405. Additionally or alternatively, the piston 430 could be driven by a low pressure (e.g., a vacuum, a suction source, an evacuated volume) beneath the piston 430.

The use of the resistive element 436 to ignite the propellant 435 is intended as a non-limiting example. Other means for igniting a chemical propellant (or some other chemical or element of the device 400 according to an application) are anticipated, including but not limited to generating an electrical spark (e.g., by applying a high voltage across a spark gap or between electrodes of the device 400), illuminating the propellant (e.g., using a laser, an LED, or some other light-emitting element(s)), applying a fore and/or vibration to the propellant (e.g., using a piezoelectric elements), or changing a pressure to which the propellant is exposed.

When suction is provided by a suction source that comprises an evacuated volume, a pressure within the evacuated volume could be specified to provide sufficient suction to draw blood into the chambers 450a, 450b. For example, the pressure within the evacuated volume could be less than approximately 50 kilopascals. Further, the device 400 could be constructed such that the evacuated volume has a pressure less than some maximum value (e.g., 50 kilopascals) for some specified minimum period of time such that the evacuated volume could be used as a suction source to draw blood into the device 400 at a specified future point in time. This could include the device 400 being made with high-quality seals and adhesives between elements of the device 400 that comprise and/or form the evacuated volume. In some examples, surface elements (e.g., the housing 410, the seal 443, the circuit board 415) of the device 400 that are joined to form the evacuated volume could have highly smooth surfaces. In some examples, the device 400 could be configured and/or assembled such that the pressure within the evacuated volume remains below a specified maximum pressure for 48 hours, a week, or some other specified period of time to permit the use of the evacuated volume to provide suction to draw blood into the device 400 at a specified future point in time that is less than the specified period of time. In some examples, this could include storing the device 400 in an evacuated volume of a package (e.g., within an evacuated and sealed blister of packaging material) and removing the device 400 from the evacuated volume of the package before mounting the device 400 to skin.

The seal 443 could be composed of a variety of materials to allow suction to be applied to and contained by the seal 443 until the seal is pierced by the needle 420. Further, the seal 443 could be composed of materials that are capable of being vacuum-formed into a specified shape (e.g., a shape that can be mounted to the housing 410 and that includes one or more concave depressions, e.g., 423). For example, the seal 443 could be composed of polycarbonate.

Note that the configurations and operations of devices as described herein are meant as non-limiting examples of operation of devices configured to puncture skin and to receive blood emitted from the skin in response to being punctured. Such devices could include a variety of means for penetrating or piercing skin, for driving such penetrating means into skin, for subsequently retracting such penetrating means from the skin, for drawing, wicking, suctioning, or otherwise receiving blood responsively emitted from the skin, for storing the received blood, for sensing a hematocrit or some other properties of the received blood, for moving, directing, preserving, or otherwise interacting with the received blood, or for performing some additional or alternative operations of functions according to an application.

III. EXAMPLE WEARABLE DEVICES

Wearable blood-accessing and/or hematocrit-detecting devices as described herein can be configured to be mounted to an external body surface of a wearer and to enable a variety of applications and functions including accessing blood of the wearer (e.g., drawing, extracting, or otherwise receiving blood), detecting a hematocrit of such accessed blood, storing such accessed blood, detecting one or more properties of such accessed blood, detecting some other properties of the body of the wearer (e.g., a pulse rate), or performing some other functions. Such wearable devices could enable a variety of applications, including measuring physiological information about a wearer, indicating such measured information or other information to the wearer (e.g., using a vibrator, a screen, a beeper), recording such information, indicating such information to a remote system (e.g., a server in a physician's office), or other functions.

Figure 5A:
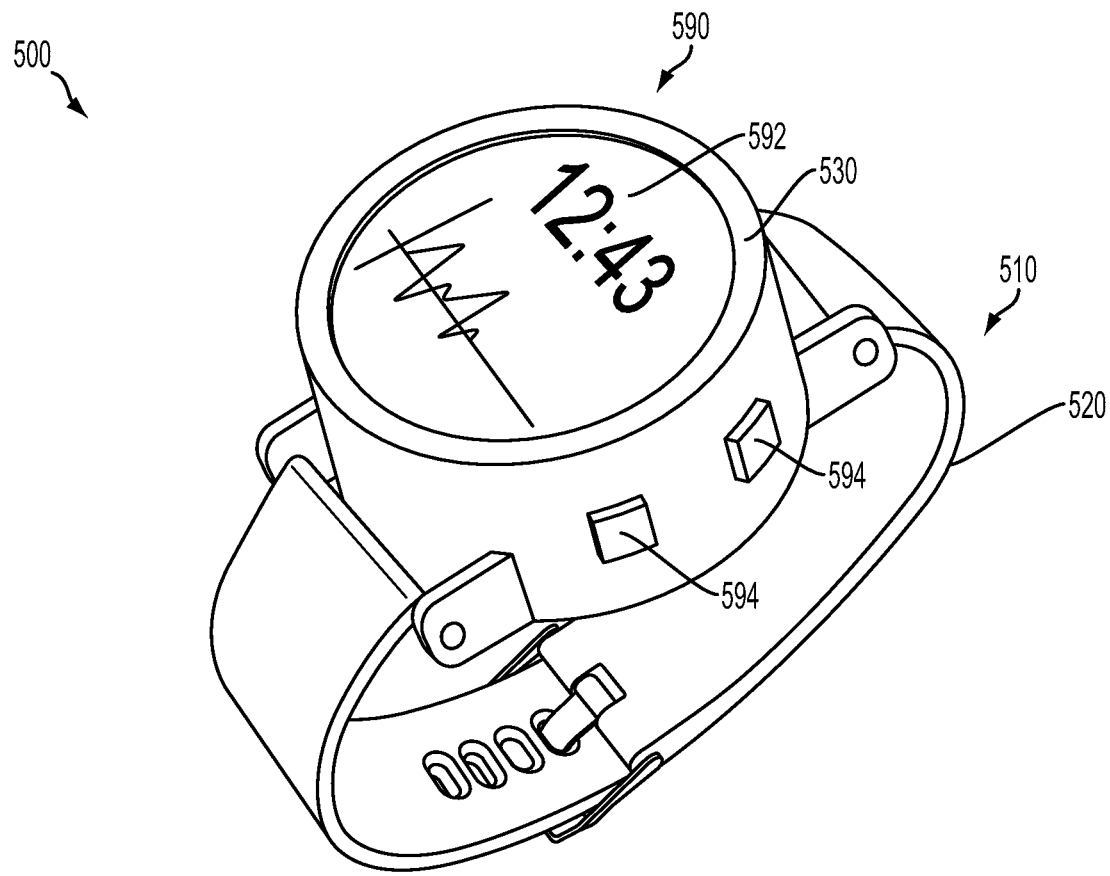
FIG. 5A is a perspective top view of an example body-mountable device.
Figure 5B:
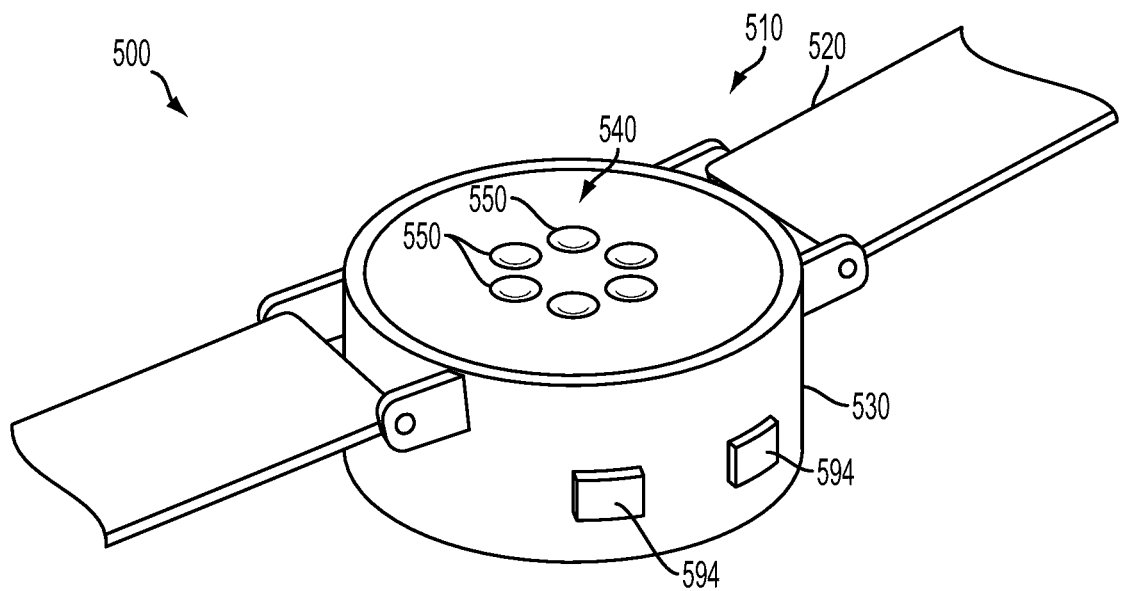
FIG. 5B is a perspective bottom view of the example body-mountable device shown in FIG. 5A.

In some examples, a wearable device 500 (illustrated in FIG. 5) is provided as a wrist-mounted device, as shown in FIGS. 5A and 5B. The wrist-mounted device 500 may be mounted to the wrist of a living subject with a wristband or cuff, similar to a watch or bracelet. The wearable device 500 can be configured to access blood of a wearer and to store, detect a hematocrit or other property of, or otherwise interact with such accessed blood. The term "wearable device," as used in this disclosure, refers to any device that is capable of being worn at, on or in proximity to a body surface, such as a wrist, ankle, waist, chest, or other body part. In order to access blood from within and/or beneath skin of the body, the wearable device may be positioned on a portion of the body where subsurface vasculature or other targets or elements of the body of the wearer are easily accessed (e.g., punctured), the qualification of which will depend on the type of system used. A mount 510, such as a belt, wristband, ankle band, etc. can be provided to mount the device at, on or in proximity to the body surface. The mount 510 may prevent the wearable device from moving relative to the body to allow for blood to be drawn from a puncture produced in the skin by the device 500 (e.g., by a driven and subsequently retracted needle of the device) or according to some other application or consideration. In one example, shown in FIGS. 5A and B, the mount 510 may take the form of a strap or band 520 that can be worn around the wrist (or some other part) of the body. Further, the mount 510 may be an adhesive substrate for adhering the blood-accessing device 500 to the body of a wearer.

A housing 530 is disposed on the mount 510 such that it can be positioned on the body. A contact surface 540 of the housing 530 is intended to be mounted facing to the external body surface. The housing 530 may include sensors for detecting one or more physiological properties of the wearer (e.g., a hematocrit, a pulse, a blood oxygenation, a galvanic skin response). The contact surface 540 additionally includes a number of concave depressions 550. Each concave depression 550 corresponds to a blood-accessing section of the device 500 that can be operated to drive a needle, through the concave depression (e.g., through a seal of the device and/or through a channel of the device configured to allow the passage of the needle), into skin of a wearer and subsequently to retract the needle from the skin. Further, each section is configured to receive blood responsively emitted from the skin (e.g., by wicking, capillary action, application of suction, or some other means) and to detect a hematocrit of, store, detect another property of, or otherwise interact with the received blood.

The housing 530 could be configured to be water-resistant and/or water-proof. That is, the housing 530 could be configured to include sealants, adhesives, gaskets, welds, transparent windows, apertures, press-fitted seams, and/or other joints such that the housing 530 is resistant to water entering an internal volume or volumes of the housing 530 when the housing 530 is exposed to water. The housing 530 could further be water-proof, i.e., resistant to water entering an internal volume or volumes of the housing 530 when the housing 530 is submerged in water. For example, the housing 530 could be water-proof to a depth of 1 meter, i.e., configured to resist water entering an internal volume or volumes of the housing 530 when the housing 530 is submerged to a depth of 1 meter.

The wearable device 500 may also include a user interface 590 via which the wearer of the device may receive one or more recommendations or alerts generated either from a remote server or other remote computing device, or from a processor within the device. The alerts could be any indication that can be noticed by the person wearing the wearable device 500. For example, the alert could include a visual component (e.g., textual or graphical information on a display), an auditory component (e.g., an alarm sound), and/or tactile component (e.g., a vibration). Further, the user interface 590 may include a display 592 where a visual indication of the alert or recommendation may be displayed. The display 592 may further be configured to provide an indication of a measured hemodynamic property of blood accessed from the body of the wearer using the device (e.g., to provide an indication of a hematocrit of the wearer's blood).

Further, the user interface 590 may include one or more buttons 594 for accepting inputs from the wearer. For example, the buttons 594 may be configured to change the text or other information visible on the display 592. The buttons 594 may be configured to accept inputs for controlling aspects of the data collection system, such as initiating a measurement period (e.g., causing the device 500 to access blood of the wearer by driving a needle into skin or according to some other method), inputs indicating the wearer's current health state (i.e., normal, migraine, shortness of breath, heart attack, fever, "flu-like" symptoms, food poisoning, etc.), or inputs indicating the wearer's activities (e.g., eating a meal, taking a medication).

Note that example devices herein are configured to be mounted to a wrist of a wearer. However, the embodiments described herein could be applied to other body parts (e.g., an ankle, a thigh, a chest, an abdomen, a forehead, a thigh, a finger), or to detect hematological properties or other physiological properties in other environments. For example, embodiments described herein could be applied to detect one or more properties in a target environment (e.g., a natural environment, an environment of an industrial, pharmaceutical, or water treatment process).

Figure 6A:
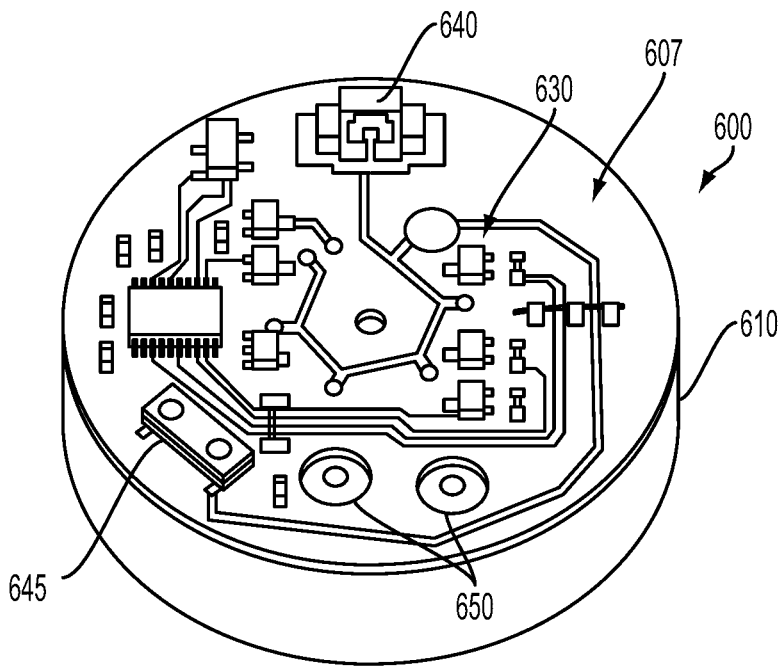
FIG. 6A is a perspective top view of an example body-mountable device.
Figure 6B:
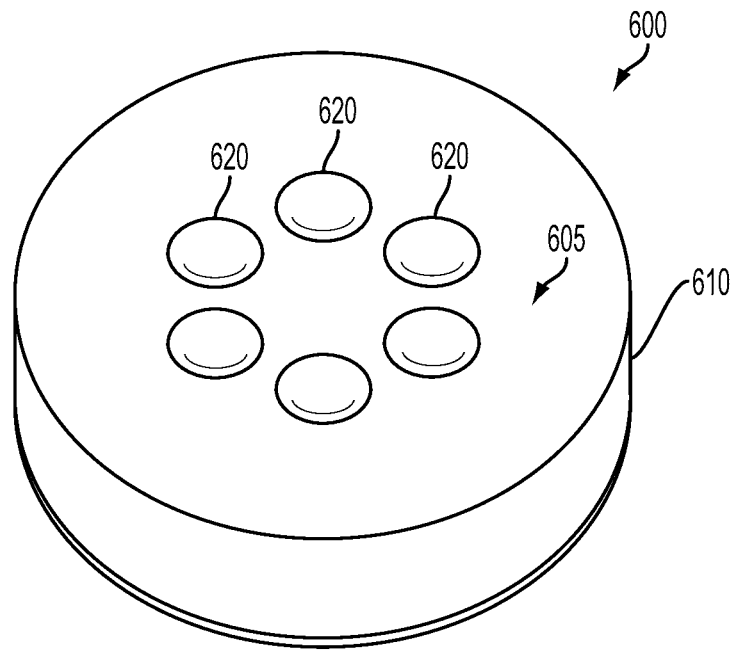
FIG. 6B is a perspective bottom view of the example body-mountable device shown in FIG. 6A.

Hematocrit sensors of the device 500, as described herein, could be single-use; for example, an injector of one or more sections could ignite a limited supply of a propellant and/or suction could be provided for/in a section by a single evacuated volume. In such examples, such single and/or limited-use blood-accessing sections could be configured to be a removable and/or replaceable element of the wearable device 500. For example, FIGS. 6A and 6B show a blood-accessing device 600 that could be configured to be removably mounted on or within the wearable device 500. The blood-accessing device 600 includes a housing 610 that can be positioned on skin of a body when the blood-accessing device 600 is mounted on or within the wearable device 500 and the wearable device 500 is mounted to the body. A contact surface 605 of the housing 610 is intended to be mounted facing to the external body surface. The contact surface 605 includes a number of concave depressions 620. Each concave depression 620 corresponds to a blood-accessing section of the blood-accessing device 600 that can be operated (e.g., when mounted on or within the wearable device 500) to drive a needle, through the concave depression (e.g., through a seal of the device and/or through a channel of the device configured to allow the passage of the needle), into skin of a wearer and subsequently to retract the needle from the skin. Further, each section is configured to receive blood responsively emitted from the skin (e.g., by wicking, capillary action, application of suction, or some other means) and to store, detect a hematocrit or other property of, or otherwise interact with the received blood.

The wearable device 500 could be configured to operate the blood-accessing device 600 to access a number of samples of blood from skin (e.g., at respective specified points in time). Once the body-mountable device has operated all of the sections of the blood-accessing device 600, the blood-accessing device 600 could be removed from the wearable device 500 and replaced. In some examples, this could include operating one or more injectors, suction sources, and/or other components of the blood-accessing device 600 (e.g., via electrical connector 640, optical receiver/transmitter 645, and/or electronics 630). Additionally or alternatively, the wearable device 500 could operate the blood-accessing device 600 using other means, e.g., by igniting propellant of the blood-accessing device 600 by heating the propellant using a laser of the wearable device 500.

In some examples, the removed blood-accessing device 600 could be configured to store blood, and blood stored in the removed blood-accessing device 600 could be presented to a sensing device for analysis (e.g., the removed blood-accessing device 600 could be sent via post to a sensing device at a laboratory that is remote from a user of the body-mountable device 500). For example, samples of blood stored within the blood-accessing device 600 could be accessed via ports 650 of the blood-accessing device 600.

Additionally or alternatively, the wearable device 500 could be configured to detect one or more properties of the blood accessed using the blood-accessing device 600. In some examples, the blood-accessing device 600 could include one or more sensors configured to detect a hematocrit or other properties of blood. The wearable device 500 could operate the sensors of the blood-accessing device 600 (e.g., via electrical connector 640, optical receiver/transmitter 645, and/or electronics 630. Additionally or alternatively, the wearable device 500 could be configured to illuminate and/or receive light emitted from the blood-accessing device 600 (e.g., to illuminate and/or receive light emitted from an analyte-sensitive chemical that has one or more optical properties that is related to the analyte in the blood), via a window, optical fiber, or other optically transparent element(s) of the blood-accessing device 600) to detect one or more properties of the blood drawn, wicked, suctioned, or otherwise received from skin by the blood-accessing device 600.

Wearable blood-accessing devices and other embodiments as described herein can include a variety of components configured in a variety of ways. Devices described herein could include electronics including a variety of different components configured in a variety of ways to enable applications of the wearable device. The electronics could include controllers, amplifiers, switches, display drivers, touch sensors, wireless communications chipsets (e.g., Bluetooth radios or other radio transceivers and associated baseband circuitry to enable wireless communications between the wearable device and some other system(s)), or other components. The electronics could include a controller configured to operate one or more sensors, injectors, suction sources, and/or components of a blood-accessing device to detect one or more hematological or other properties of a body and/or to access and store or otherwise interact with blood from within and/or beneath skin of the body. The controller could include a processor configured to execute computer-readable instructions (e.g., program instructions stored in data storage of the wearable device) to enable applications of the wearable device. The electronics can include additional or alternative components according to an application of the wearable device.

Wearable or otherwise-configured blood-accessing devices as described herein could include one or more user interfaces. A user interface could include a display configured to present an image to a wearer and to detect one or more finger presses of a wearer on the interface. The controller or some other component(s) of the electronics could operate the user interface to provide information to a wearer or other user of the device and to enable the wearer or other user to affect the operation of the wearable device, to determine some property of the wearable device and/or of the wearer of the wearable device (e.g., a hematocrit of blood and/or a health state of a wearer of the wearable device), or to provide some other functionality or application to the wearer and/or user. As one example, the wearer could press an indicated region of the user interface to indicate that the wearable device should begin logging detected medical information about the wearer. Other indicated information, changes in operation of the wearable device, or other functions and applications of the user interface are anticipated.

Note that the embodiments illustrated in the Figures are illustrative examples and not meant to be limiting. Alternative embodiments, including more or fewer components in alternative configurations are anticipated. A wearable, handheld, body-mountable, desktop, or otherwise configured device could include multiple housings or other such assemblies each containing some set of components to enable applications of such a device. A blood-accessing device as described herein could be configured to perform a variety of functions and to enable a variety of applications. Blood-accessing devices could be configured to operate in concert with other devices or systems; for example, blood-accessing devices could include a wireless communication interface configured to transmit data indicative of one or more properties of the blood of a wearer of the wearable device. Other embodiments, operations, configurations, and applications of a blood-accessing device as described herein are anticipated.

FIG. 7 is a simplified schematic of a system including one or more wearable blood-accessing and/or hematocrit-detecting devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In some examples, multiple wearable devices 700 could be configured to access blood from and/or detect multiple hematological or other properties of a single wearer. For example, the single wearer could wear or otherwise operate two or more wearable devices 700 to measure respective hematological or other physiological properties from respective two or more portions of the body of the wearer (e.g., respective portions of subsurface vasculature of the wearer) and/or during different periods of time (e.g., the wearable devices 700 used by the wearer could be limited-use devices, e.g., each including a discrete number of single-use blood-accessing sections).

In addition to receiving communications from the wearable device 700, such as collected hematological properties or other collected physiological properties and data regarding health state as input by the user and/or one or more properties of a wearer detected using a sensor disposed in the wearable device 700, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the hematological property data and the indicated health state of the user. From this information, the server may be configured to derive an indication of the effectiveness of the drug or treatment. For example, if a drug is intended to control a blood sugar of a wearer and the wearer of the device does not indicate that they are experiencing nausea, lightheadedness, or other sequelae after beginning a course of treatment with the drug, the server may be configured to derive an indication that the drug is effective for that wearer.

Further, some embodiments of the system may include privacy controls which may be automatically implemented or controlled by the wearer of the device. For example, where a wearer's collected hematological property data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and hematological properties, collected from his or her device may only be used for generating an individual baseline and recommendations in response to collection and comparison of his or her own data and may not be used in generating a population baseline or for use in population correlation studies.

IV. EXAMPLE ELECTRONICS

Figure 8:
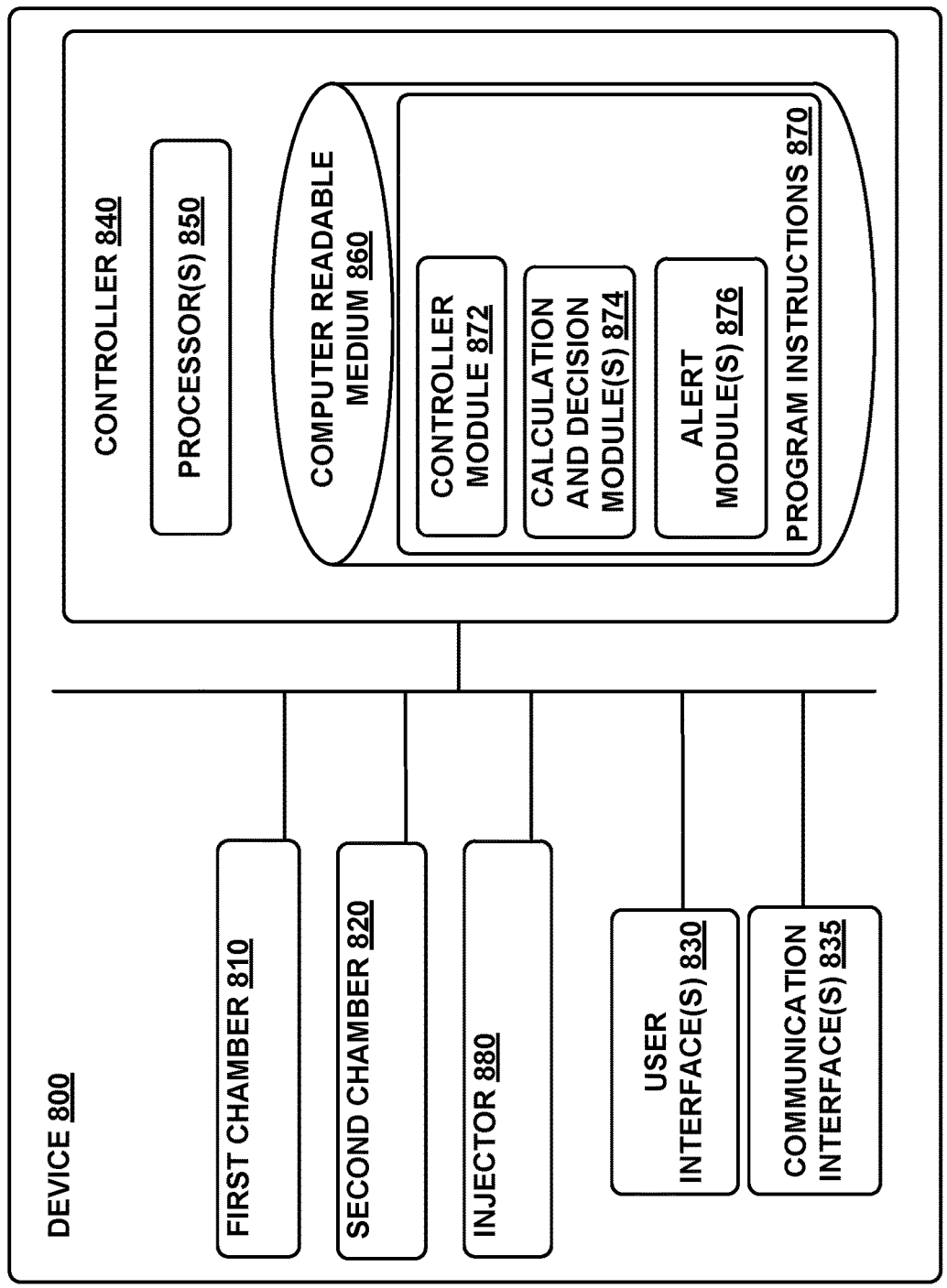
FIG. 8 is a functional block diagram of an example device.

FIG. 8 is a simplified block diagram illustrating the components of a device 800, according to an example embodiment. Device 800 may take the form of or be similar to one of the hematocrit-detecting devices 100, 200, 300a, 30b, 400, 500, 600 shown in FIGS. 1A-C, 2A-C, 3A, 3B, 4A-D, 5A-B, and 6A-B. However, device 800 may also take other forms, such as an ankle, waist, or chest-mounted device. Device 800 could also take the form of a device that is not configured to be mounted to a body. For example, device 800 could take the form of a handheld device configured to be maintained in proximity to skin or some other source of a blood sample by a user or operator of the device 800 or by a frame or other supporting structure. In other examples, the device 800 could be part of another system configured to access and/or provide a volume of blood to the device 800, e.g., part of a syringe, a dialysis machine, a catheter, or some other device or system. Device 800 also could take other forms.

In particular, FIG. 8 shows an example of a device 800 having first 810 and second 820 chambers having respective electrodes, an injector 880, a user interface 830, communication interface 835 for transmitting data to a remote system, and a controller 840. The components of the device 800 may be disposed on a mount or on some other structure for mounting the device to enable stable reception of blood, e.g., stable collection of blood emitted from skin in response to a penetration of the skin by one or more needles of the device 800, for example, mounting to an external body surface where one or more portions of subsurface vasculature or other anatomical elements are readily accessible.

Controller 840 may be provided as a computing device that includes one or more processors 850. The one or more processors 850 can be configured to execute computer-readable program instructions 870 that are stored in the computer readable data storage 860 and that are executable to provide the functionality of a device 800 described herein. Alternatively, the controller 840 could include other electronics (e.g., oscillators, amplifiers, buffers, envelope detectors, operational amplifiers) configured to operate the injector 880, to detect impedances of fluids contained within the chambers 810, 820, to determine a hematocrit based on such detected impedances, or to perform some other operations.

The computer readable medium 860 may include or take the form of one or more non-transitory, computer-readable storage media that can be read or accessed by at least one processor 850. The one or more computer-readable storage media can include volatile and/or non-volatile storage components, such as optical, magnetic, organic or other memory or disc storage, which can be integrated in whole or in part with at least one of the one or more processors 850. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

First 810 and second 820 chambers could include respective electrodes and other elements configured to receive respective different portions of a volume of blood (e.g., a whole-blood portion and a plasma-only portion) and to use the electrodes to detect the impedance of such fluid portions. The injector 880 could include any components configured to drive a needle into skin, to subsequently retract the needle from the skin, and to perform other functions as described elsewhere herein. The chambers 810, 820 and/or injector 880 could be part of a removable and/or replaceable portion of the device 800. The device 800 may include further sensors (not shown), e.g., heart rate sensors, galvanic skin response sensors, pulse oximeters, or other sensors configured to detect one or more properties of the body of a wearer and/or of the environment of the device 800.

The program instructions 870 stored on the computer readable medium 860 may include instructions to perform any of the methods described herein. For instance, in the illustrated embodiment, program instructions 870 include a controller module 872, calculation and decision module 874 and an alert module 876.

Calculation and decision module 874 may include instructions for operating the chambers 810, 820 and/or injector 880 and analyzing data generated by the chambers 810, 820 to detect impedances of portions of blood in the chambers and/or to determine a hematocrit of blood or other information (e.g., health states) of a body of a wearer of the device 800. For example, calculation and decision module 874 can include instructions to apply an alternating current through electrodes of the chambers 810, 820 and measuring responsively generated voltages of the electrodes in order to detect impedances of fluids in the chambers 810, 820. Calculation and decision module 874 could additionally include instructions to determine a hematocrit of blood based on such determined impedances, e.g., based on a ratio of the detected impedances.

Calculation and decision module 874 can additionally include instructions for analyzing the data to determine if a medical condition or other specified condition is indicated, or other analytical processes relating to the environment proximate to the device 800 (e.g., based on information generated by additional sensors of the device 800). In particular, the calculation and decision module 874 may include instructions for operating the injector 880 to access blood (e.g., for operating resistive heating elements of the injector 880 to ignite propellant and drive a needle into skin) at respective specified points in time (e.g., points in time while a wearer sleeps, points in time during the week).

The controller module 872 can also include instructions for operating a user interface 830. For example, controller module 872 may include instructions for displaying data collected by the blood-accessing sections 810, 820 and analyzed by the calculation and decision module 874, or for displaying one or more alerts generated by the alert module 876. Controller module 872 may include instructions for displaying data related to a detected hematological property of accessed blood and/or a determined health state of a wearer. Further, controller module 872 may include instructions to execute certain functions based on inputs accepted by the user interface 830, such as inputs accepted by one or more buttons disposed on the user interface.

Communication platform 835 may also be operated by instructions within the controller module 872, such as instructions for sending and/or receiving information via a wireless antenna, which may be disposed on or in the device 800. The communication interface 835 can optionally include one or more oscillators, mixers, frequency injectors, etc. to modulate and/or demodulate information on a carrier frequency to be transmitted and/or received by the antenna. In some examples, the device 800 is configured to indicate an output from the processor by modulating an impedance of the antenna in a manner that is perceivable by a remote server or other remote computing device.

The program instructions of the calculation and decision module 874 may, in some examples, be stored in a computer-readable medium and executed by a processor located external to the device 800. For example, the device 800 could be configured to collect certain data regarding hematological properties from the user and then transmit the data to a remote server, which may include a mobile device, a personal computer, the cloud, or any other remote system, for further processing.

The computer readable medium 860 may further contain other data or information, such as medical and health history of a user of the device 800, that may be useful in determining whether a medical condition or some other specified condition is indicated. Further, the computer readable medium 860 may contain data corresponding to certain physiological parameter baselines (e.g., hematocrit values), above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the user of the device 800 based on data collected based on a certain number of blood samples accessed using blood-accessing elements (e.g., 810, 820) of the device 800. Baselines may also be generated by a remote server and transmitted to the device 800 via communication interface 830. The calculation and decision module 874 may also, upon determining that a medical or other emergency condition is indicated, generate one or more recommendations for the user of the device 800 based, at least in part, on consultation of a clinical protocol. Such recommendations may alternatively be generated by the remote server and transmitted to the device 800.

In some examples, the collected hematological property data, baseline profiles, health state information input by device users and generated recommendations and clinical protocols may additionally be input to a cloud network and be made available for download by a user's physician. Trend and other analyses may also be performed on the collected data, such as hemodynamic property data and health state information, in the cloud computing network and be made available for download by physicians or clinicians.

Further, hematological property and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical or other specified condition is indicated (e.g., that a wearer is hyperglycemic or hypoglycemic, based on a detected glucose level of blood accessed from the body of the wearer), the alert module 876 may generate an alert via the user interface 830. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, deliver a dose of a pharmaceutical (e.g., insulin), seek immediate medical attention, or administer a medication.

The controller 840 could additionally or alternatively include analog components, non-programmable components, or other electronics that do not include a processor and that are configured to detect impedances of fluids in the chambers 810, 820, to determine a hematocrit value and/or other signal based on such detected impedance values, to operate the injector 880, or to perform other operations. For example, the controller 840 could include one or more oscillators and/or current-controlled amplifiers configured to, when the controller receives electrical power and/or control signals, apply an alternating current at a specified frequency and/or amplitude to electrodes of the chambers 810, 820. Such a controller 840 could further include buffers, amplifiers, envelope detectors, or other elements to generate signals related to the impedances of fluids in the chambers 810, 820 based on alternating voltages exhibited between electrodes of the chambers 810, 820 in response to the application of the alternative current. Such a controller 840 could yet further include operational amplifiers or other components to generate signals related to the ratio of the impedances of the fluids in the chambers 810, 820, to the hematocrit of blood received by the device 800, or related to some other variable of interest.

V. EXAMPLE METHODS

Figure 9:
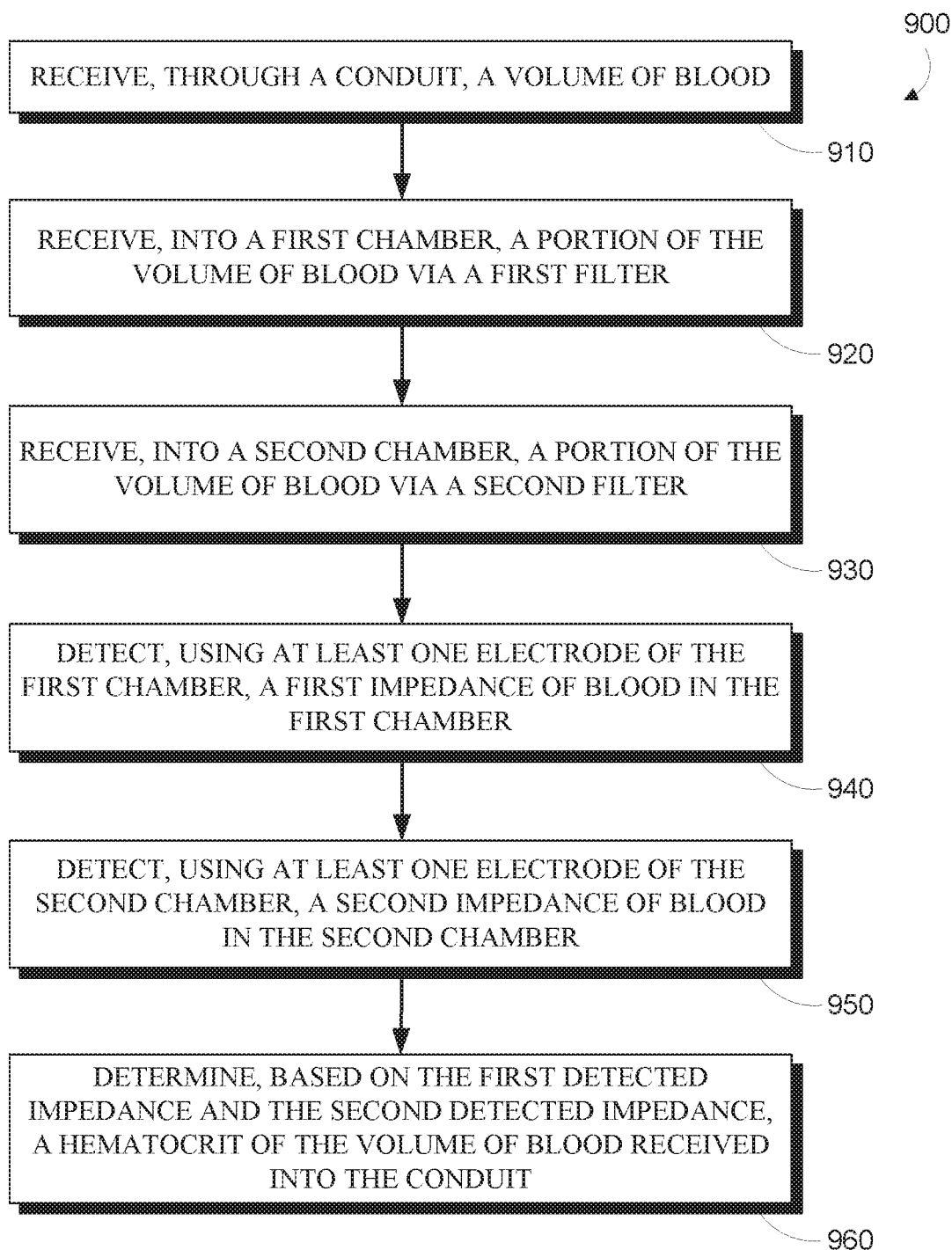
FIG. 9 is a flowchart of an example method.

FIG. 9 is a flowchart of a method 900 for measuring a hematocrit of blood using a system as described herein. The system includes: (i) a conduit, (ii) a first chamber that comprises at least one electrode, (iii) a first filter that comprises a material that blocks passage of red blood cells, (iv) a second chamber that comprises at least one electrode, (v) a second filter that comprises a material that blocks passage of red blood cells and that has at least one hole through which red blood cells can pass. The system could be a wearable device, a handheld device, a desktop device, a wall- or ceiling-mounted device, or some other form of device.

The method 900 includes receiving, through the conduit, a volume of blood (910). This could include applying a suction source to draw the blood into the conduit. Such a suction source could include a pump or an evacuated volume, e.g., an evacuated volume that includes the conduit and/or other elements of the system. Applying suction could include breaking a seal between such an evacuated volume an environment, e.g., by operating an injector to penetrate the seal with a needle. Additionally or alternatively, the conduit could include hydrophobic and/or hydrophilic materials configured to draw the volume of blood into the conduit.

The method 900 additionally includes receiving, into the first chamber, a portion of the volume of blood via the first filter (920). This could include providing suction to the first chamber, e.g., via a gas-permeable membrane. Additionally or alternatively, a hydrophilic material (e.g., a mesh composed of hydrophilic material) could be disposed within the first chamber to draw the portion of blood into the first chamber. Receiving a portion of blood into the second chamber (920) could include additional or alternative steps or features.

The method 900 additionally includes receiving, into the second chamber, a portion of the volume of blood via the second filter (930). This could include providing suction to the second chamber, e.g., via a gas-permeable membrane. Additionally or alternatively, a hydrophilic material (e.g., a mesh composed of hydrophilic material) could be disposed within the second chamber to draw the portion of blood into the second chamber. Receiving a portion of blood into the second chamber (930) could include additional or alternative steps or features.

The method 900 further includes detecting, using at least one electrode of the first chamber, a first impedance of blood in the first chamber (940). This could include applying an alternative current at a specified frequency and amplitude into the portion of blood in the first chamber using the at least one electrode in the first chamber. For example, an alternating current having a frequency greater than 15 kilohertz could be applied through the at least one electrode of the first chamber. An amplitude or other properties of a voltage between the at least one electrode of the first chamber and some other electrode (e.g., another electrode disposed in the first chamber or an electrode disposed in some other location and in electrical contact with a portion of the volume of blood received into the hematocrit sensor) could be detected and used to determine an impedance of the portion of blood in the first chamber.

The method 900 further includes detecting, using at least one electrode of the second chamber, a second impedance of blood in the second chamber (950). This could include applying an alternative current at a specified frequency and amplitude into the portion of blood in the second chamber using the at least one electrode in the second chamber. For example, an alternating current having a frequency greater than 15 kilohertz could be applied through the at least one electrode of the second chamber. An amplitude or other properties of a voltage between the at least one electrode of the second chamber and some other electrode (e.g., another electrode disposed in the second chamber or an electrode disposed in some other location and in electrical contact with a portion of the volume of blood received into the hematocrit sensor) could be detected and used to determine an impedance of the portion of blood in the second chamber.

The method 900 additionally includes determining, based on the first detected impedance and the second detected impedance, a hematocrit of the volume of blood received into the conduit (960). This could include using a lookup table, linear function, nonlinear function, or some other method to determine the hematocrit based on the first and second impedances. In some examples, this (960) could include determining a ratio of the first and second impedances and using the determine ratio to determine the hematocrit. For example, the ratio could be determined and used, according to a linear model (e.g., the ratio could be scaled and an offset added), to determine a hematocrit.

The method 900 could include additional or alternative steps. For example, the system could further include: (i) a needle configured to penetrate skin, (ii) an injector, (iii) a suction source, and (iv) a seal configured to receive suction provided by the suction source. In such an example, the method 900 could include operating the injector to drive the needle into the skin through a seal and subsequently to retract the needle to form at least one hole in the seal through which the suction source can draw blood. This could include operating the injector at a specified point in time and/or in response to a command (e.g., a command received through a user interface of the system, a command generated by the system in reasons to detecting that skin is present proximate the system, a command generated by a remote system in communication with the blood-accessing system). Operating the injector could include igniting a propellant, e.g., by heating the propellant using a resistive heating element. Additionally or alternatively, operating the injector could include operating a motor, solenoid, piezoelectric transducer, or other elements of the system and/or of the injector.

The method 900 could include heating, applying suction to, or otherwise preparing a portion of skin to emit blood in response to being pierced by a needle of the system. In some examples, the method 900 could include transmitting (e.g., wirelessly transmitting, transmitting via a Bluetooth wireless link, transmitting via a cable, transmitting via the internet or some other network) information indicative of a detected hematocrit or other property of blood accessed by the system. In some examples, the method 900 could include determining a health state of the wearer based on a hematological property detected from blood accessed by the system. In some examples, the method 900 could include indicating a detected hematological properties to a user via a user interface of the system and/or indicating such information to a remote system (e.g., to a physician's computer, via a wireless or other communications link).

The example method 900 illustrated in FIG. 9 is meant as an illustrative, non-limiting example. Additional or alternative elements of the method and additional or alternative components of the system are anticipated, as will be obvious to one skilled in the art.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein. Further, embodiments described herein in relation to the measurement of the hematocrit of a blood sample could be adapted to the measurement of the fraction of the volume of other fluid samples that is occupied by solid or semi-solid contents of such fluids.

What is claimed is:

1. A system comprising:
   a conduit;
   a first filter in fluid communication with the conduit, wherein the first filter comprises a material that blocks passage of red blood cells;
   a second filter in fluid communication with the conduit, wherein the second filter comprises a material that blocks passage of red blood cells, and wherein the second filter has at least one hole in the material through which red blood cells can pass;
   a first chamber in fluid communication with the conduit via the first filter, wherein the first chamber comprises at least one electrode; and
   a second chamber in fluid communication with the conduit via the second filter, wherein the second chamber comprises at least one electrode.

2. The system of claim 1, further comprising a controller that is operably coupled to the at least one electrode of the first chamber and the at least one electrode of the second chamber, wherein the controller comprises electronics to:
   detect, using the at least one electrode of the first chamber, a first impedance of blood in the first chamber, wherein the blood in the first chamber comprises a first portion of a volume of blood received into the conduit;
   detect, using the at least one electrode of the second chamber, a second impedance of blood in the second chamber, wherein the blood in the second chamber comprises a second portion of the volume of blood received into the conduit; and
   determine, based on the first detected impedance and the second detected impedance, a hematocrit of the volume of blood received into the conduit.

3. The system of claim 1, wherein a hydrophilic material is disposed within at least one of the first chamber or the second chamber, wherein the hydrophilic material provides a capillary force to draw blood into the at least one of the first chamber or the second chamber via the conduit.

4. The system of claim 3, wherein the first chamber and the second chamber comprise respective vents allowing for the displacement of gas from the first chamber and the second chamber when blood enters the first chamber and the second chamber from the conduit.

5. The system of claim 1, further comprising a suction source, wherein the suction source provides a suction to draw blood into each of the first chamber and the second chamber via the conduit.

6. The system of claim 5, wherein the first chamber and the second chamber comprise a first gas-permeable membrane and a second gas-permeable membrane, respectively, wherein the first and second gas-permeable membranes are not permeable to blood plasma, and wherein at least a portion of the provided suction is provided to the first and second chambers via the first and second gas-permeable membranes.

7. The system of claim 5, wherein the suction source comprises an evacuated volume, wherein the evacuated volume comprises the first chamber and the second chamber, and wherein the system further comprises:
   a needle;
   an injector, wherein the injector is operable to drive the needle into the skin to form a puncture in the skin and subsequently to retract the needle from the skin; and
   a seal, wherein the injector drives the needle through the seal to form at least one hole in the seal, and wherein the suction provided by the suction source draws blood from the formed puncture in the skin into the conduit through the formed at least one hole in the seal.

8. The system of claim 5, wherein the suction source comprises an evacuated volume, wherein the evacuated volume comprises the first chamber and the second chamber, wherein the evacuated volume further comprises a first evacuated volume and a second evacuated volume, wherein the first evacuated volume applies suction to the first chamber, wherein the second evacuated volume applies suction to the second chamber, and wherein the first and second evacuated volumes have respective sizes.

9. The system of claim 1, further comprising an anticoagulant substance disposed within at least one of the conduit, the first chamber, the second chamber, the first filter, or the second filter.

10. A method comprising:
    receiving, through a conduit, a volume of blood;
    receiving, into a first chamber, a portion of the volume of blood via a first filter, wherein the first chamber comprises at least one electrode, and wherein the first filter comprises a material that blocks passage of red blood cells;
    receiving, into a second chamber, a portion of the volume of blood via a second filter, wherein the second chamber comprises at least one electrode, wherein the second filter comprises a material that blocks passage of red blood cells, and wherein the second filter has at least one hole in the material through which red blood cells can pass;
    detecting, using the at least one electrode of the first chamber, a first impedance of blood in the first chamber;
    detecting, using the at least one electrode of the second chamber, a second impedance of blood in the second chamber; and
    determining, based on the first detected impedance and the second detected impedance, a hematocrit of the volume of blood received into the conduit.

11. The method of claim 10, wherein detecting, using the at least one electrode of the first chamber, a first impedance of blood in the first chamber comprises applying an alternating current via the at least one electrode of the first chamber.

12. The method of claim 10, wherein determining, based on the first detected impedance and the second detected impedance, a hematocrit of the volume of blood received into the conduit comprises determining a ratio of the first detected impedance and the second detected impedance.

13. The method of claim 10, wherein a hydrophilic material is disposed within at least one of the first chamber or the second chamber, wherein the hydrophilic material provides a capillary force to draw blood into the at least one of the first chamber or the second chamber from the conduit.

14. The method of claim 10, further comprising:
    operating an injector to drive a needle into skin to form a puncture in the skin and subsequently to retract the needle from the skin, wherein operating the injector to drive the needle into the skin further comprises driving the needle through a seal to form at least one hole in the seal, and wherein suction is provided by a suction source to draw the volume of blood from the formed puncture in the skin through the formed at least one hole in the seal into the conduit.

15. The method of claim 14, wherein the injector comprises:
    (a) a chamber, wherein the needle is disposed at least partially within the chamber, (b) a piston disposed in the chamber, wherein the needle is coupled to the piston, and wherein the piston can slidably move within the chamber, and (c) a propellant, wherein operating the injector to drive the needle into the skin comprises igniting the propellant to slidably move the piston within the chamber to drive the needle to pierce the seal and further to drive the needle into skin.

16. A system comprising:

a conduit;

a first filter in fluid communication with the conduit, wherein the first filter comprises a material that blocks passage of red blood cells;

a second filter in fluid communication with the conduit, wherein the second filter comprises a material that blocks passage of red blood cells, wherein the second filter has at least one hole in the material through which red blood cells can pass;

a first chamber in fluid communication with the conduit via the first filter, wherein the first chamber comprises at least one electrode;

a second chamber in fluid communication with the conduit via the second filter, wherein the second chamber comprises at least one electrode;

a needle;

an injector, wherein the injector is operable to drive the needle into skin to form a puncture in the skin and subsequently to retract the needle from the skin;

a suction source; and a seal, wherein the injector drives the needle through the seal to form at least one hole in the seal, and wherein the suction provided by the suction source draws the volume of blood from the formed puncture in the skin into the conduit through the formed at least one hole in the seal.

17. The system of claim 16, wherein the injector comprises:

a chamber, wherein the needle is disposed at least partially within the chamber;

a piston disposed in the chamber, wherein the needle is coupled to the piston, and wherein the piston is configured to slidably move within the chamber; and a propellant, wherein the propellant can slidably move the piston within the chamber to drive the needle to pierce the seal and further to drive the needle into skin.

18. The system of claim 17, wherein the propellant comprises nitrocellulose, and wherein the injector driving the needle into skin comprises the injector igniting the nitrocellulose.

19. The system of claim 16, wherein the system comprises a body-mountable device, wherein the system further comprises a controller that is operably coupled to the injector, the at least one electrode of the first chamber, and the at least one electrode of the second chamber, wherein the controller comprises electronics to:

operate the injector to drive the needle into the skin;

detect, using the at least one electrode of the first chamber, a first impedance of blood in the first chamber, wherein the blood in the first chamber comprises a portion of a volume of blood received into the conduit;

detect, using the at least one electrode of the second chamber, a second impedance of blood in the second chamber, wherein the blood in the second chamber comprises a portion of the volume of blood received into the conduit; and determine, based on the first detected impedance and the second detected impedance, a hematocrit of the volume of blood received into the conduit.

20. The system of claim 19, wherein determining, based on the first detected impedance and the second detected impedance, a hematocrit of the volume of blood received into the conduit comprises determining a ratio of the first detected impedance and the second detected impedance.

* * * * *